United States Patent
Fadli et al.

(10) Patent No.: US 8,623,100 B2
(45) Date of Patent: Jan. 7, 2014

(54) 4-AMINOINDOLE DERIVATIVES AND USE THEREOF FOR THE OXIDATION DYEING OF KERATIN FIBRES

(75) Inventors: Aziz Fadli, Chelles (FR); Fatima Makhlouf, Tremblay en France (FR)

(73) Assignee: L'Oreal, Paris (FR)

( * ) Notice: Subject to any disclaimer, the term of this patent is extended or adjusted under 35 U.S.C. 154(b) by 0 days.

(21) Appl. No.: 13/994,288

(22) PCT Filed: Dec. 14, 2011

(86) PCT No.: PCT/EP2011/072672
§ 371 (c)(1),
(2), (4) Date: Jun. 14, 2013

(87) PCT Pub. No.: WO2012/080288
PCT Pub. Date: Jun. 21, 2012

(65) Prior Publication Data
US 2013/0263390 A1 Oct. 10, 2013

Related U.S. Application Data

(60) Provisional application No. 61/432,727, filed on Jan. 14, 2011.

(30) Foreign Application Priority Data

Dec. 17, 2010 (FR) ..................... 10 60765

(51) Int. Cl.
*A61Q 5/10* (2006.01)
*C07D 209/04* (2006.01)

(52) U.S. Cl.
USPC ............ 8/405; 8/406; 8/408; 8/409; 8/574; 548/490

(58) Field of Classification Search
USPC ............ 8/405, 406, 408, 409, 574; 548/490
See application file for complete search history.

(56) References Cited

U.S. PATENT DOCUMENTS

| | | | |
|---|---|---|---|
| 4,003,699 A | 1/1977 | Rose et al. | |
| RE30,199 E | 1/1980 | Rose et al. | |
| 4,823,985 A | 4/1989 | Grollier et al. | |
| 5,061,289 A | 10/1991 | Clausen et al. | |
| 5,254,135 A * | 10/1993 | Lang et al. | 8/408 |
| 5,380,340 A | 1/1995 | Neunhoeffer et al. | |
| 5,534,267 A | 7/1996 | Neunhoeffer et al. | |
| 5,663,366 A | 9/1997 | Neunhoeffer et al. | |
| 5,766,576 A | 6/1998 | Löwe et al. | |
| 5,938,792 A | 8/1999 | Lang et al. | |
| 6,099,592 A | 8/2000 | Vidal et al. | |
| 6,099,593 A | 8/2000 | Terranova et al. | |
| 6,284,003 B1 | 9/2001 | Rose et al. | |
| 6,338,741 B1 | 1/2002 | Vidal et al. | |
| 6,645,258 B2 | 11/2003 | Vidal et al. | |
| 6,730,789 B1 | 5/2004 | Birault et al. | |
| 2002/0050013 A1 | 5/2002 | Vidal et al. | |
| 2003/0019051 A9 | 1/2003 | Vidal et al. | |
| 2003/0167579 A1 | 9/2003 | Lang | |

FOREIGN PATENT DOCUMENTS

| | | |
|---|---|---|
| DE | 23 59 399 | 6/1975 |
| DE | 38 43 892 | 6/1990 |
| DE | 41 33 957 | 4/1993 |
| DE | 195 43 988 | 5/1997 |
| EP | 0 425 345 | 5/1991 |
| EP | 0 770 375 | 5/1997 |
| FR | 2 586 913 | 3/1987 |
| FR | 2 733 749 | 11/1996 |
| FR | 2 750 048 | 12/1997 |
| FR | 2 801 308 | 5/2001 |
| FR | 2 805 739 | 9/2001 |
| FR | 2 886 136 | 12/2006 |
| GB | 1 026 978 | 4/1966 |
| GB | 1 153 196 | 5/1969 |

(Continued)

OTHER PUBLICATIONS

STIC Search Report dated Jul. 25, 2013.*

(Continued)

*Primary Examiner* — Eisa Elhilo
(74) *Attorney, Agent, or Firm* — O'Brien Jones, PLLC.

(57) ABSTRACT

The invention relates to 4-aminoindole derivatives of formula (I), and the addition salts thereof, mesomers thereof, isomers thereof and solvates thereof: and to their use for the oxidation dyeing of keratin fibers, and in particular of human keratin fibers such as the hair. The present invention makes it possible to achieve dark shades, natural shades and dark natural shades. The present invention also makes it possible to obtain powerful, chromatic, aesthetic, sparingly selective coloration of keratin fibers in varied shades, which is resistant to the various attacking factors to which the hair may be subjected. In particular, when the 4-aminoindole derivatives are combined with one or more heterocyclic oxidation bases, they make it possible to obtain a wide range of colors and coloration of keratin fibers that shows good chromaticity and good selectivity.

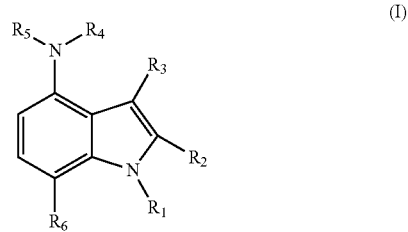

(I)

16 Claims, No Drawings

(56) References Cited

FOREIGN PATENT DOCUMENTS

| | | |
|---|---|---|
| JP | 2-19576 | 1/1990 |
| JP | 05-163124 | 6/1993 |
| WO | 92/18093 | 10/1992 |
| WO | 94/08969 | 4/1994 |
| WO | 94/08970 | 4/1994 |
| WO | 96/15765 | 5/1996 |
| WO | 03/031436 | 4/2003 |
| WO | 2008/153730 | 12/2008 |

OTHER PUBLICATIONS

International Search Report for PCT/EP2011/072672, (2012).

* cited by examiner

4-AMINOINDOLE DERIVATIVES AND USE THEREOF FOR THE OXIDATION DYEING OF KERATIN FIBRES

This is a national stage application of PCT/EP2011/072672, filed internationally on Dec. 14, 2011, which claims priority to U.S. Provisional Application No. 61/432,727, filed on Jan. 14, 2011; as well as French Application FR 1060765, filed on Dec. 17, 2010.

The invention relates to 4-aminoindole derivatives, and to their use for the oxidation dyeing of keratin fibres, and in particular human keratin fibres such as the hair.

It is known practice to dye keratin fibres, and in particular human keratin fibres such as the hair, with dye compositions comprising oxidation dye precursors, in particular ortho- or para-phenylenediamines, ortho- or para-aminophenols, heterocyclic compounds such as diaminopyrazole derivatives, pyrazolo[1,5-a]pyrimidine derivatives, pyrimidine derivatives, pyridine derivatives, 5,6-dihydroxyindole derivatives and 5,6-dihydroxyindoline derivatives, which are generally known as oxidation bases. Oxidation dye precursors, or oxidation bases, are colourless or weakly coloured compounds, which, when combined with oxidizing products, can give rise to coloured compounds or dyes by a process of oxidative condensation.

It is also known that the shades obtained with these oxidation bases may be varied by combining them with couplers or coloration modifiers, the latter being chosen especially from meta-phenylenediamines, meta-aminophenols, meta-hydroxyphenols and certain heterocyclic compounds, for instance pyrazolo[1,5-b]-1,2,4-triazole derivatives, pyrazolo[3,2-c]-1,2,4-triazole derivatives, pyrazolo[1,5-a]pyrimidine derivatives, pyridine derivatives, pyrazol-5-one derivatives, indoline derivatives and indole derivatives.

The variety of molecules used as oxidation bases and couplers allows a wide range of colours to be obtained.

The "permanent" coloration obtained by means of these oxidation dyes must moreover satisfy a certain number of requirements. Thus it should have no toxicological drawbacks, it should allow shades to be obtained in the desired intensity, and it should show good resistance to external agents such as light, bad weather, washing, permanent waving treatments, perspiration and rubbing.

The dyes should also allow grey hair to be covered and, finally, they should be as unselective as possible, i.e. they should produce the smallest possible differences in coloration along the same keratin fibre, which in fact may be differently sensitized (i.e. damaged) between its end and its root. They must also show good chemical stability in the formulations. They must have a good toxicological profile.

Documents EP 0 425 345 and WO 92/18093 disclose the use of derivatives of aminoindole type and in particular 7-methyl-1H-indol-4-amine and 7-ethyl-1H-indol-4-amine as oxidation dyes for the dyeing of keratin fibres.

However, the prior art couplers are not entirely satisfactory in terms of solubility, uptake and dyeing properties.

In particular, when the prior art couplers are combined with heterocyclic bases that afford a wide range of colours, the coloration obtained occasionally lacks chromaticity, fastness and/or selectivity.

The aim of the present invention is to provide novel couplers that do not have the drawbacks of the couplers known in the prior art, and in particular couplers that can produce a coloration in varied shades, which is powerful, chromatic, aesthetic, sparingly selective and resistant to the various attacking factors to which the hair may be subjected, such as shampooing, light, sweat and permanent reshaping.

One subject of the present invention is thus 4-aminoindole derivatives of formula (I), and the addition salts thereof, mesomers thereof, isomers thereof and solvates thereof:

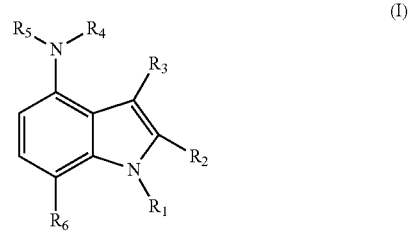

(I)

in which:

$R_1$ represents:
- a hydrogen atom;
- a linear or branched saturated $C_1$-$C_6$ alkyl radical, optionally interrupted with an oxygen atom or a radical $NR_7$, optionally substituted with a radical chosen from OH and $NR_7R_8$;

$R_2$ and $R_3$, which may be identical or different, represent:
- a hydrogen atom;
- a $C_1$-$C_6$ and preferably $C_1$-$C_4$ alkyl radical, optionally substituted with one or more hydroxyl radicals;
- a carboxyl radical;
- a radical $CONR_7R_8$;

$R_4$ and $R_5$, which may be identical or different, represent:
- a hydrogen atom;
- a $C_1$-$C_6$ alkyl radical;

$R_6$ represents:
- a linear or branched $C_1$-$C_6$ alkyl radical, optionally interrupted with a heteroatom chosen from O or a radical $NR_9$, and/or optionally substituted with one or more radicals, which may be identical or different, chosen from OH and $NR_7R_8$;
- a carboxyl radical;
- a $C_1$-$C_{10}$ alkyl carboxylate;
- a radical $CONR_7R_8$;
- a $C_1$-$C_{10}$ (poly)hydroxyalkoxy;
- a radical (poly)($C_1$-$C_{10}$)alkoxy($C_1$-$C_{10}$)alkyloxy;
- a radical O-Ak-$NR_9R_{10}$ with Ak=linear $C_1$-$C_8$ or branched $C_3$-$C_8$ divalent alkylene radical, optionally interrupted with one or more oxygen atoms and/or groups $NR_7$;

$R_7$ and $R_8$, which may be identical or different, represent:
- a hydrogen atom;
- a $C_1$-$C_8$ alkyl radical optionally substituted with one or more hydroxyl radicals;

$R_9$ and $R_{10}$, which may be identical or different, represent a linear or branched, saturated or unsaturated $C_1$-$C_4$ alkyl;

$R_9$ and $R_{10}$ may form, with the nitrogen that bears them, a saturated or unsaturated 5- to 8-membered heterocycle, one of the chain members possibly being an oxygen atom or a radical $NR_{11}$ with $R_{11}$=H or $C_1$-$C_4$ alkyl, optionally substituted with one or more radicals chosen from OH and $NR_7R_8$; with the exception of the following two compounds:

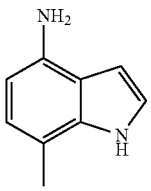

7-methyl-1H-
indol-4-amine

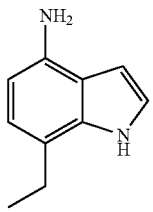

7-ethyl-1H-
indol-4-amine

The present invention makes it possible to achieve dark shades, natural shades and dark natural shades.

The present invention also makes it possible to obtain powerful, chromatic, aesthetic, sparingly selective coloration of keratin fibres in varied shades, which is resistant to the various attacking factors to which the hair may be subjected, such as shampooing, light, sweat and permanent reshaping.

In particular, the combination of the 4-aminoindole derivatives as defined above with one or more heterocyclic oxidation bases makes it possible to obtain a wide range of colours and coloration of keratin fibres that shows good chromaticity and good selectivity.

A subject of the present invention is also the use of a 4-aminoindole derivative of formula (I), an addition salt thereof, a mesomer thereof, an isomer thereof or a solvate thereof for the oxidation dyeing of keratin fibres.

A subject of the present invention is also a composition for the oxidation dyeing of keratin fibres, comprising at least one coupler chosen from the 4-aminoindole derivatives of formula (I) as defined previously, the addition salts thereof, mesomers thereof, isomers thereof and solvates thereof.

Another subject of the invention is a process for dyeing keratin fibers using this composition.

Unless otherwise indicated, the limits of the ranges of values that are given in the context of the present invention are included in these ranges.

In the context of the invention, unless otherwise indicated, the alkyl radicals are linear or branched. An alkoxy radical is a radical alkyl-O—, the alkyl radical being as defined previously.

According to one particular embodiment of the invention, $R_1$ represents a hydrogen atom or a saturated $C_1$-$C_4$ alkyl radical optionally substituted with a hydroxyl radical.

According to another particular embodiment, $R_2$ and $R_3$, which may be identical or different, represent a hydrogen atom; a $C_1$-$C_4$ alkyl radical optionally substituted with one or more hydroxyl radicals; a carboxyl radical; a radical $CONR_7R_8$, preferably $CONH_2$.

According to another particular embodiment, $R_4$ and $R_5$ are identical and represent a hydrogen atom.

According to another particular embodiment, $R_6$ represents a linear or branched $C_1$-$C_6$ alkyl radical; a carboxyl radical; a $C_1$-$C_6$ alkyl carboxylate; a carboxamide radical; a $(C_1$-$C_6)$alkoxy$(C_1$-$C_6)$alkyloxy radical; a $C_1$-$C_6$ hydroxyalkyloxy radical; a radical O-Ak-$NR_9R_{10}$ with Ak=linear $C_1$-$C_6$ or branched $C_3$-$C_6$ divalent alkylene radical optionally interrupted with a radical $NR_7$.

According to one particular embodiment, the compounds in accordance with the invention are chosen from the 4-aminoindole derivatives of formula (I'), and also the addition salts thereof, mesomers thereof, isomers thereof and solvates thereof:

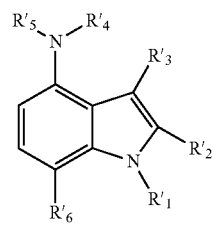

in which:
$R'_1$ represents:
  a hydrogen atom;
  a saturated $C_1$-$C_4$ alkyl radical optionally substituted with a hydroxyl radical;
$R'_2$ and $R'_3$, which may be identical or different, represent:
  a hydrogen atom;
  a $C_1$-$C_4$ alkyl radical optionally substituted with one or more hydroxyl radicals, preferably optionally substituted with a hydroxyl radical;
  a carboxyl radical;
  a radical $CONR'_7R'_8$, preferably a carboxamide radical $CONH_2$;
$R'_4$ and $R'_5$ represent a hydrogen atom;
$R'_6$ represents:
  a linear or branched $C_1$-$C_6$ alkyl radical;
  a carboxyl radical;
  a $C_1$-$C_6$ alkyl carboxylate;
  a carboxamide radical;
  a radical $(C_1$-$C_6)$alkoxy$(C_1$-$C_6)$alkyloxy;
  a $C_1$-$C_6$ hydroxyalkoxy;
  a radical O-Ak-$NR'_9R'_{10}$ with Ak=linear $C_1$-$C_6$ or branched $C_3$-$C_6$ divalent alkylene radical, optionally interrupted with one or more oxygen atoms and/or groups $NR'_7$;
$R'_7$ and $R'_8$ represent a hydrogen atom or a $C_1$-$C_6$ alkyl radical optionally substituted with a hydroxyl radical;
$R'_9$ and $R'_{10}$, which may be identical or different, represent a saturated linear $C_1$-$C_4$ alkyl radical or an unsaturated linear $C_2$-$C_4$ alkyl radical;
$R'_9$ and $R'_{10}$ may form, with the nitrogen that bears them, a saturated or unsaturated 5- to 8-membered heterocycle, one of the chain members possibly being an oxygen atom or a radical $NR'_{11}$ with $R'_{11}$=H or $C_1$-$C_4$ alkyl, optionally substituted with OH;
with the exception of the following two compounds:

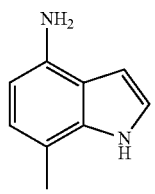

7-methyl-1H-
indol-4-amine

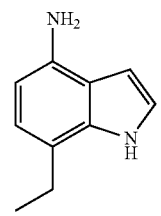

7-ethyl-1H-
indol-4-amine

The derivatives of formula (I) in accordance with the invention may be optionally salified with strong mineral acids, for instance HCl, HBr, HI, H₂SO₄ or H₃PO₄, or organic acids, for instance acetic acid, lactic acid, tartaric acid, citric acid, succinic acid, benzenesulfonic acid, para-toluenesulfonic acid, formic acid or methanesulfonic acid.

The derivatives of formula (I) in accordance with the invention may also be in the form of solvates, for example a hydrate or a solvate of a linear or branched alcohol such as ethanol or isopropanol.

In the context of the invention, the term "derivatives of formula (I)" means any mesomeric or isomeric form.

As examples of derivatives of formula (I) in accordance with the invention, mention may be made of the compounds presented below:

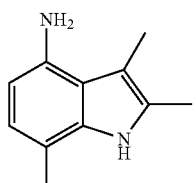

2,3-dimethyl-7-(propan-2-yl)-1H-indol-4-amine

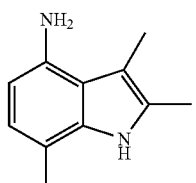

7-ethyl-2,3-dimethyl-1H-indol-4-amine

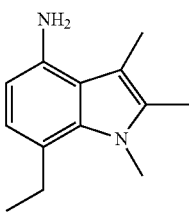

7-ethyl-1,2,3-trimethyl-1H-indol-4-amine

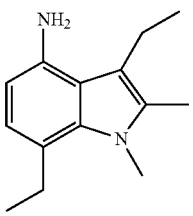

3,7-diethyl-1,2-dimethyl-1H-indol-4-amine

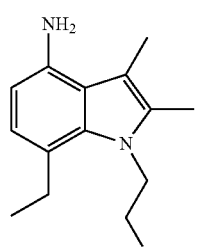

2,3,7-trimethyl-1H-indol-4-amine

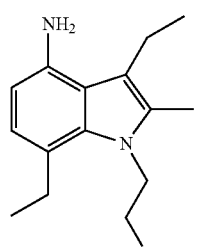

3-ethyl-2,7-dimethyl-1H-indol-4-amine

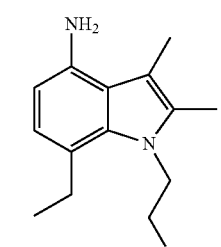

2-(4-amino-7-ethyl-2,3-dimethyl-1H-indol-1-yl)ethanol

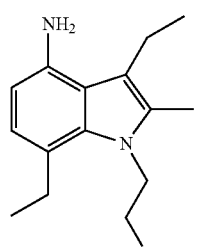

2-(4-amino-3,7-diethyl-2-methyl-1H-indol-1-yl)ethanol

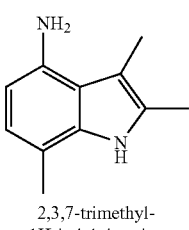

7-ethyl-2,3-dimethyl-1H-indol-4-amine

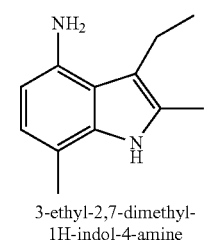

3,7-diethyl-2-methyl-1H-indol-4-amine

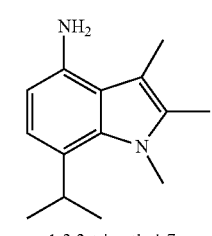

1,2,3-trimethyl-7-(propan)-2-yl)-1H-indol-4-amine

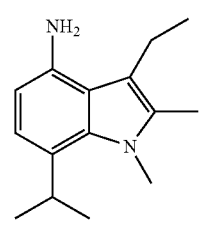

3-ethyl-1,2-dimethyl-7-(propan-2-yl)-1H-indol-4-amine

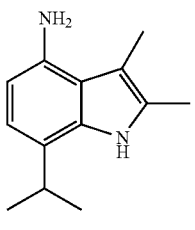

2,3-dimethyl-7-(propan-2-yl)-1H-indol-4-amine

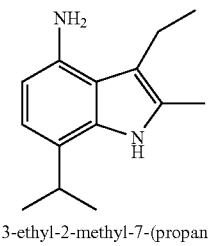

3-ethyl-2-methyl-7-(propan)-2-yl)-1H-indol-4-amine

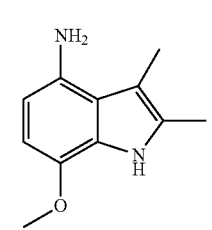

2-[4-amino-2,3-dimethyl-7-propan-2-yl)-1H-indol-1-yl]ethanol

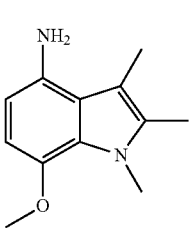

2-[4-amino-3-ethyl-2-methyl-7-propan-2-yl)-1H-indol-1-yl]ethanol 7-methoxy-2,3-dimethyl-1H-indol-4-amine 7-methoxy-1,2,3-trimethyl-1H-indol-4-amine

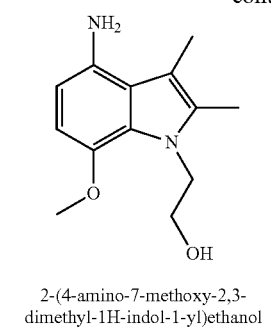

2-(4-amino-7-methoxy-2,3-dimethyl-1H-indol-1-yl)ethanol

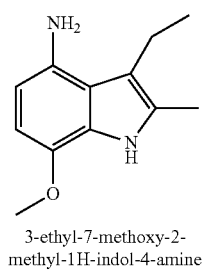

3-ethyl-7-methoxy-2-methyl-1H-indol-4-amine

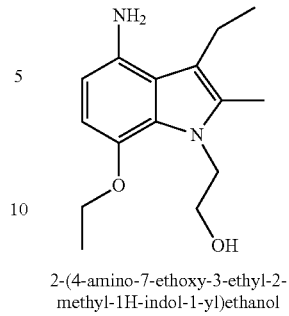

2-(4-amino-7-ethoxy-3-ethyl-2-methyl-1H-indol-1-yl)ethanol

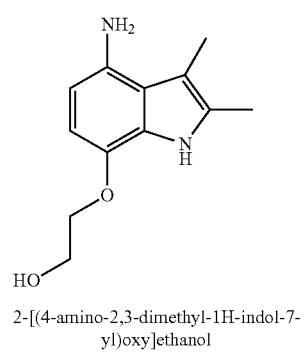

2-[(4-amino-2,3-dimethyl-1H-indol-7-yl)oxy]ethanol

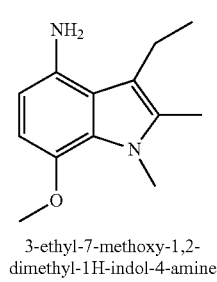

3-ethyl-7-methoxy-1,2-dimethyl-1H-indol-4-amine

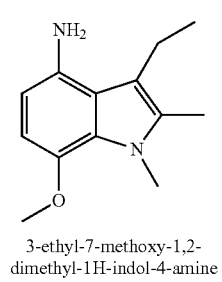

3-ethyl-7-methoxy-1,2-dimethyl-1H-indol-4-amine

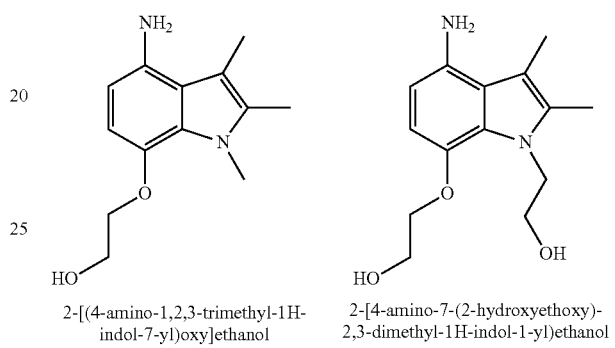

2-[(4-amino-1,2,3-trimethyl-1H-indol-7-yl)oxy]ethanol

2-[4-amino-7-(2-hydroxyethoxy)-2,3-dimethyl-1H-indol-1-yl]ethanol

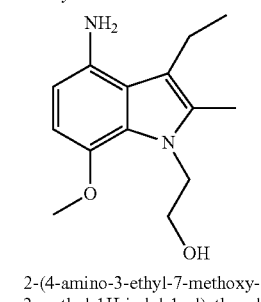

2-(4-amino-3-ethyl-7-methoxy-2-methyl-1H-indol-1-yl)ethanol

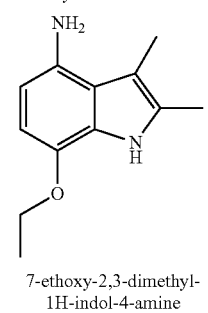

7-ethoxy-2,3-dimethyl-1H-indol-4-amine

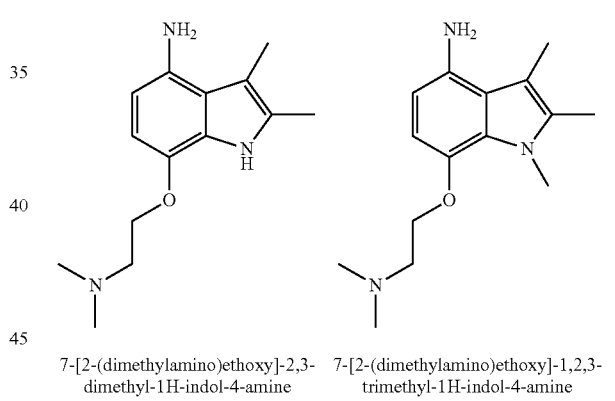

7-[2-(dimethylamino)ethoxy]-2,3-dimethyl-1H-indol-4-amine

7-[2-(dimethylamino)ethoxy]-1,2,3-trimethyl-1H-indol-4-amine

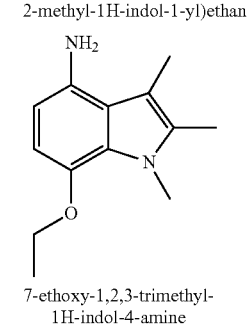

7-ethoxy-1,2,3-trimethyl-1H-indol-4-amine

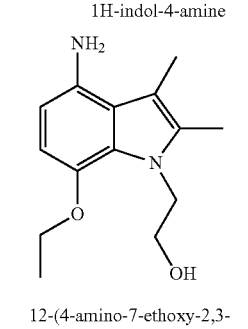

12-(4-amino-7-ethoxy-2,3-dimethyl-1H-indol-1-yl)ethanol

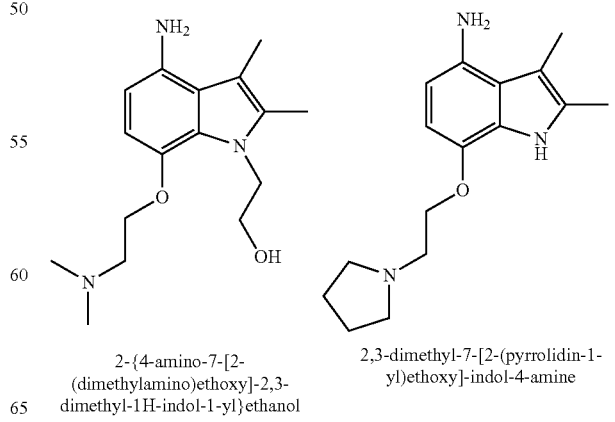

2-{4-amino-7-[2-(dimethylamino)ethoxy]-2,3-dimethyl-1H-indol-1-yl}ethanol 2,3-dimethyl-7-[2-(pyrrolidin-1-yl)ethoxy]-indol-4-amine

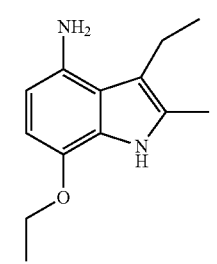

7-ethoxy-3-ethyl-2-methyl-1H-indol-4-amine

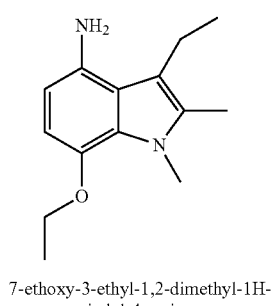

7-ethoxy-3-ethyl-1,2-dimethyl-1H-indol-4-amine

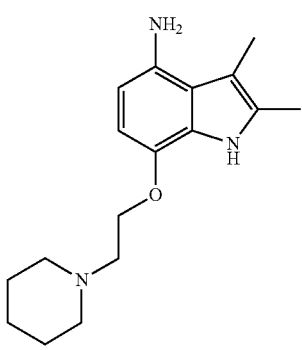

2,3-dimethyl-7-[2-(piperidin-1-yl)ethoxy]-1H-indol-4-amine

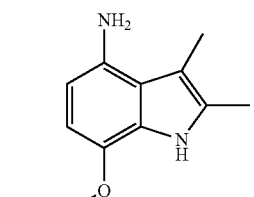

2-(4-{2-[(4-amino-2,3-dimethyl-1H-indol-7-yl)oxy]ethyl}piperazin-1-yl)ethanol

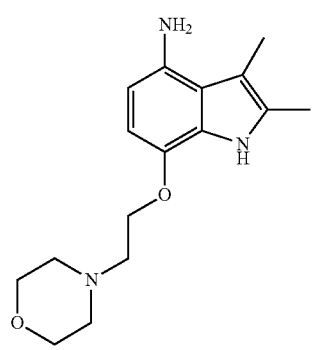

2,3-dimethyl-7-[2-(morpholin-4-yl)ethoxy]-1H-indol-4-amine

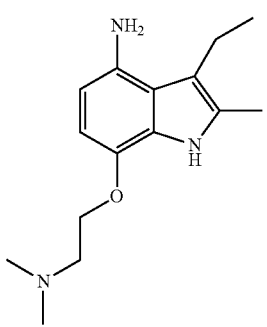

7-[2-(dimethylamino)ethoxy]-3-ethyl-2-methyl-1H-indol-4-amine

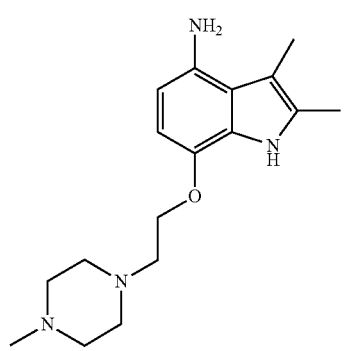

2,3-dimethyl-7-[2-(4-methylpiperazin-1-yl)ethoxy]-1H-indol-4-amine

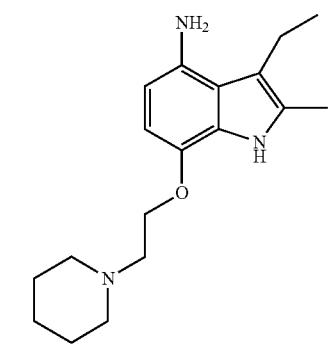

3-ethyl-2-methyl-7-[2-(piperidin-1-yl)ethoxy]-1H-indol-4-amine

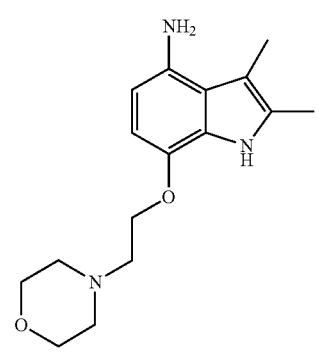

2,3-dimethyl-7-[2-(morpholin-4-yl)ethoxy]-1H-indol-4-amine

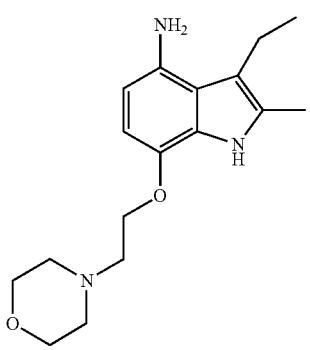

3-ethyl-2-methyl-7-[2-(morpholin-4-yl)ethoxy]-1H-indol-4-amine

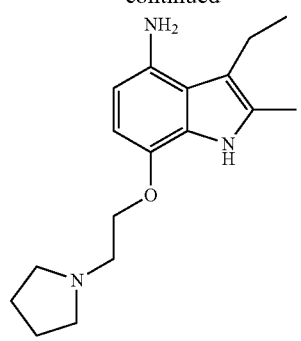
3-ethyl-2-methyl-7-[2-(pyrrolidin-1-yl)ethoxy]-
1H-indol-4-amine
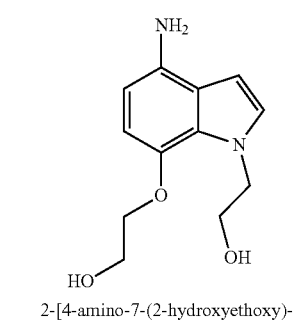
2-[4-amino-7-(2-hydroxyethoxy)-
1H-indol-1-yl]ethanol
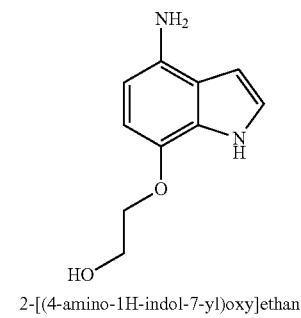
2-[(4-amino-1H-indol-7-yl)oxy]ethanol
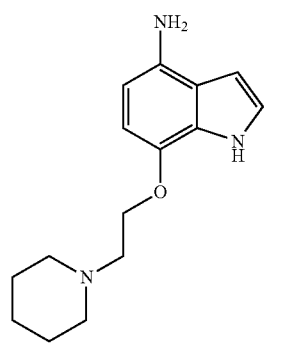
7-[2-piperidin-1-yl)ethoxy]-1H-indol-4-amine
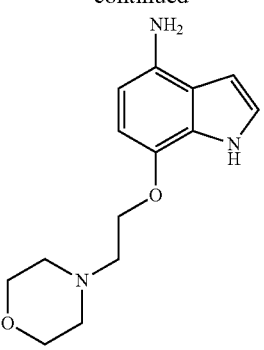
7-[2-(morpholin-4-yl)ethoxy]-1H-indol-4-amine
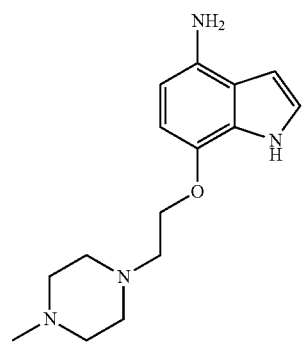
7-[2-(4-methylpiperazin-1-yl)ethoxy]-
1H-indol-4-amine
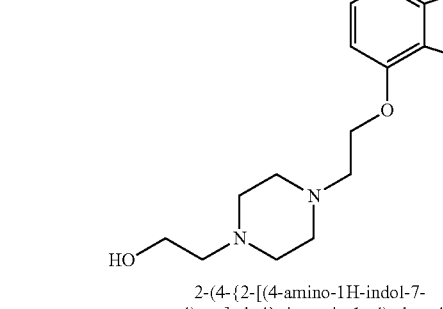
2-(4-{2-[(4-amino-1H-indol-7-
yl)oxy]ethyl}piperazin-1-yl)ethanol
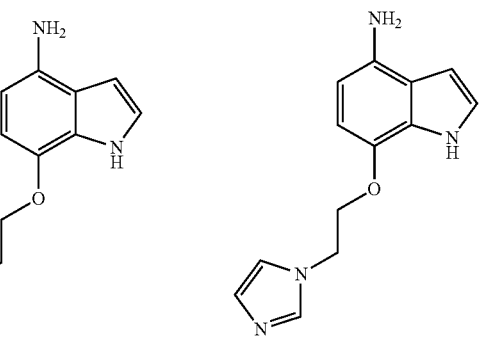
7-[2-(dimethylamino)ethoxy]-
1H-indol-4-amine
7-[2-(1H-imidazol-1-yl)ethoxy]-
1H-indol-4-amine -continued

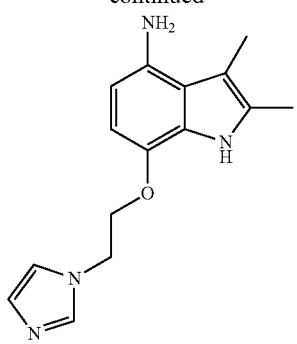
7-[2-(1H-imidazol-1-yl)ethoxy]-2,3-dimethyl-1H-indol-4-amine

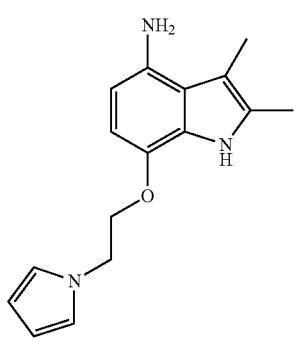
2,3-dimethyl-7-[2-(1H-pyrrol-1-yl)ethoxy]-1H-indol-4-amine

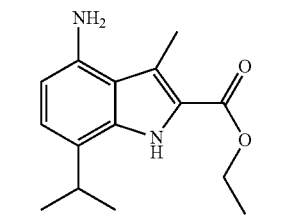
ethyl 4-amino-3-methyl-7-(propan-2-yl)-1H-indole-2-carboxylate

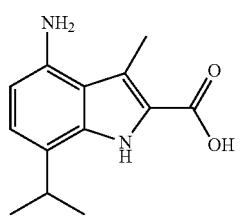
4-amino-7-(propan-2-yl)-1H-indole-2-carboxylic acid

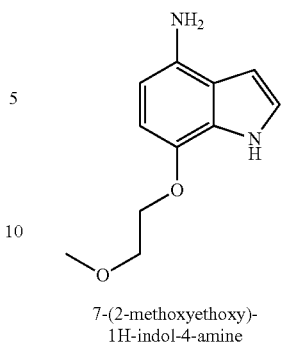
7-(2-methoxyethoxy)-1H-indol-4-amine

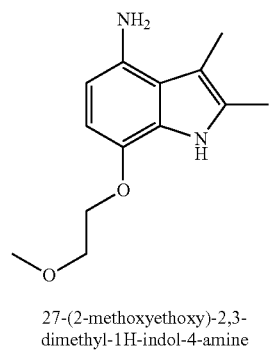
27-(2-methoxyethoxy)-2,3-dimethyl-1H-indol-4-amine

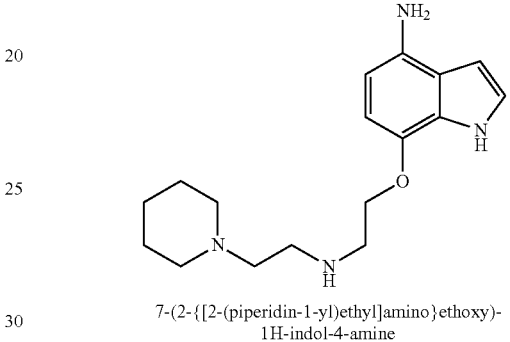
7-(2-{[2-(piperidin-1-yl)ethyl]amino}ethoxy)-1H-indol-4-amine

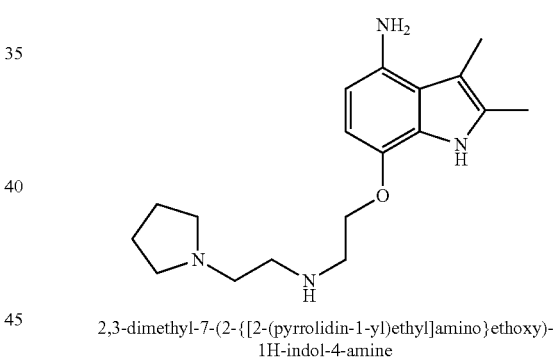
2,3-dimethyl-7-(2-{[2-(pyrrolidin-1-yl)ethyl]amino}ethoxy)-1H-indol-4-amine

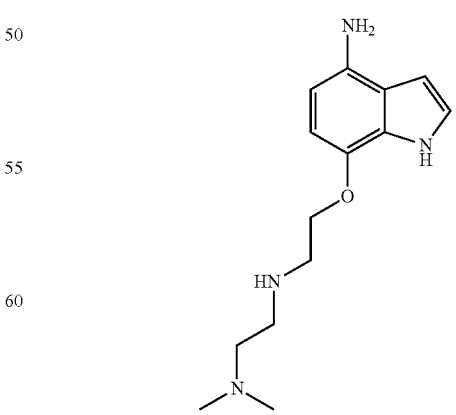
N'-{2-[(4-amino-1H-indol-7-yl)oxy]ethyl}-N,N-dimethylethane-1,2-diamine

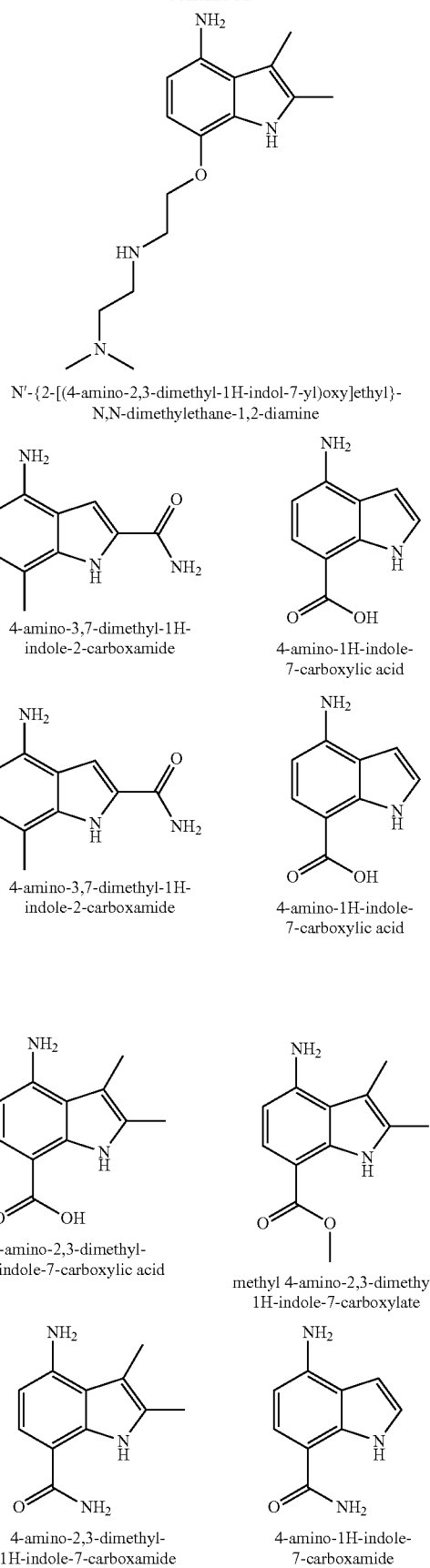
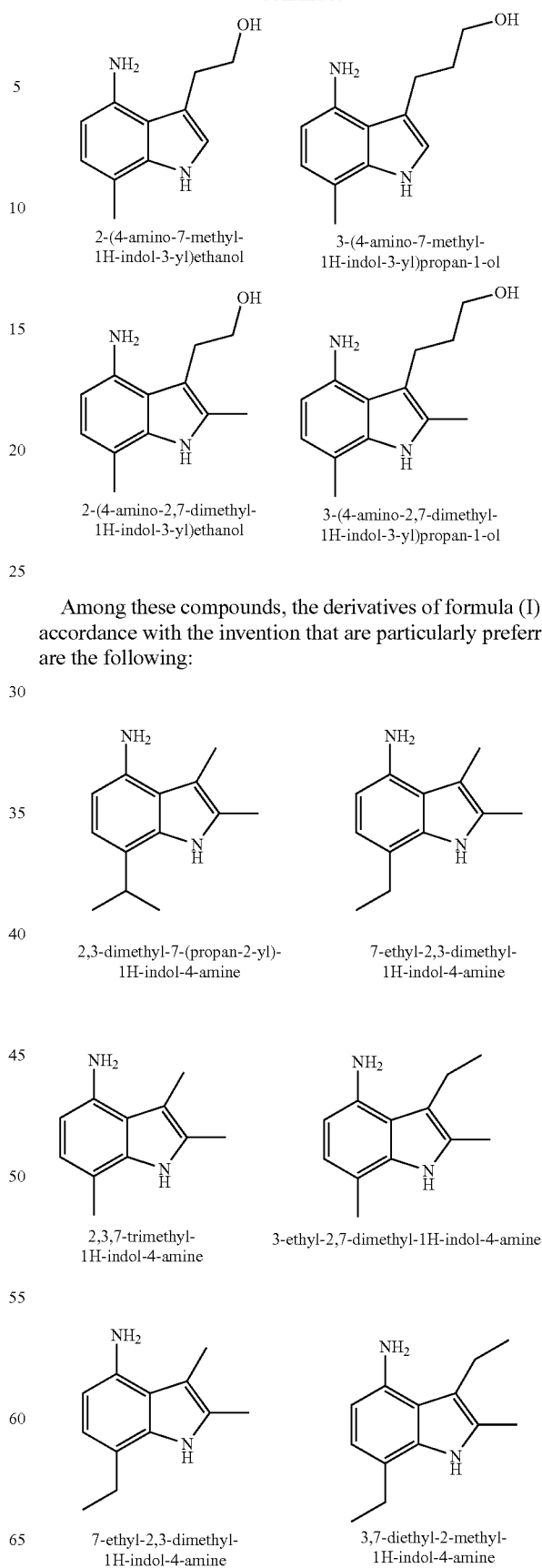
Among these compounds, the derivatives of formula (I) in accordance with the invention that are particularly preferred are the following:

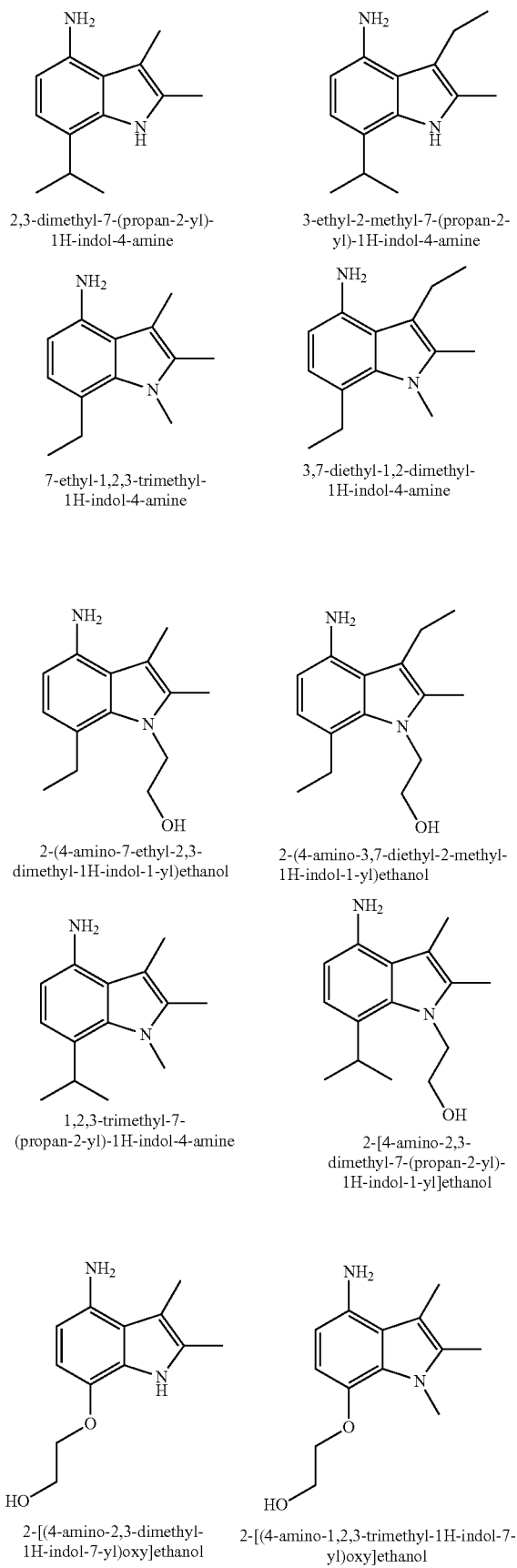
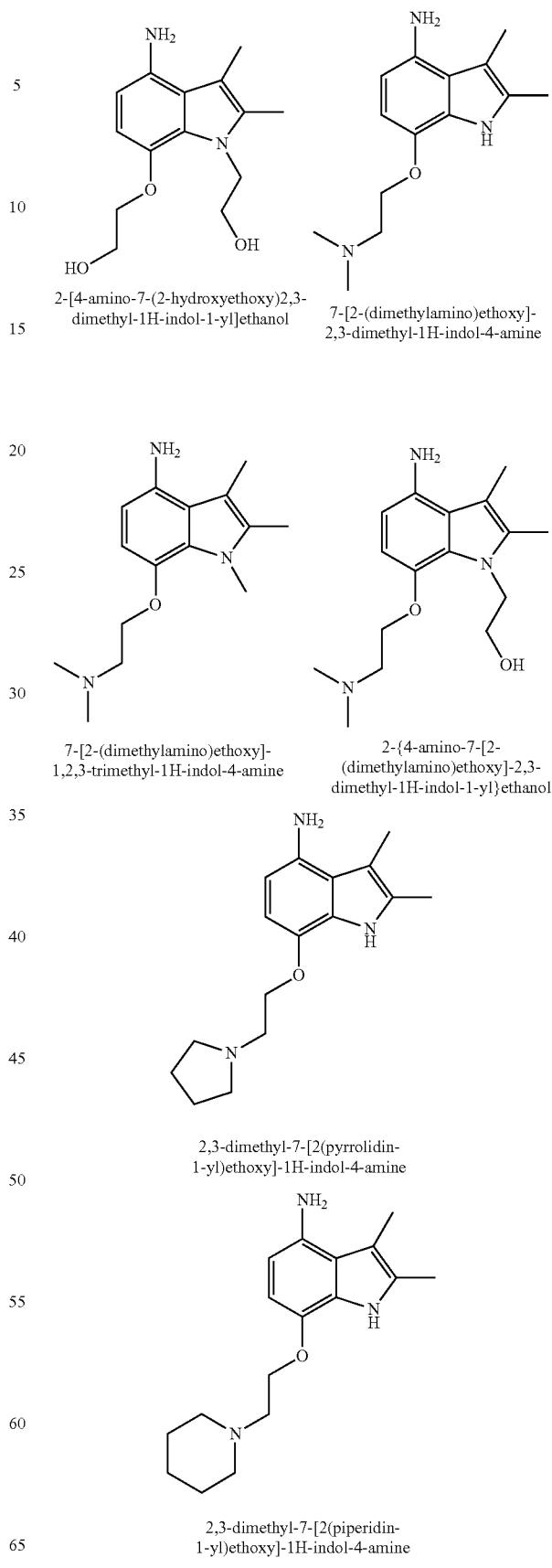

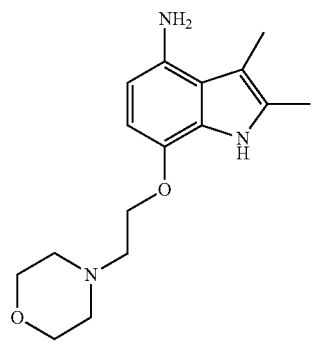

2,3-dimethyl-7-[2(morpholin-4-yl)ethoxy]-1H-indol-4-amine

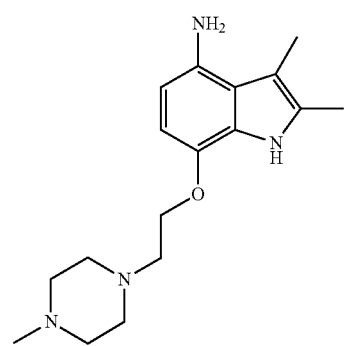

2,3-dimethyl-7-[2-(4-methylpiperazin-1-yl)ethoxy]-1H-indol-4-amine

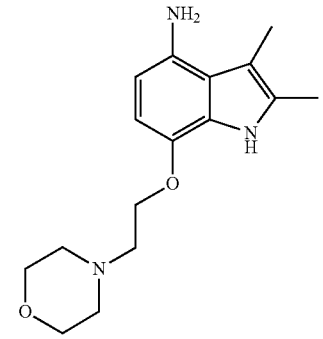

2,3-dimethyl-7-[2-(4-morpholin-4-yl)ethoxy]-1H-indol-4-amine

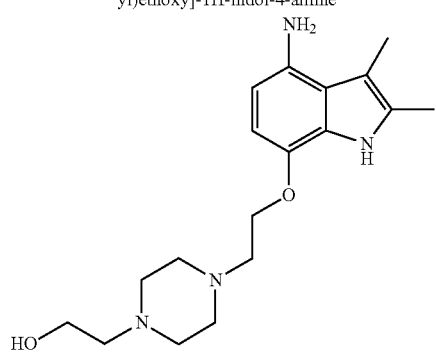

2-(4-{2-[(4-amino-2,3-dimethyl-1H-indol-7-yl)oxy]ethyl}piperazin-1-yl)ethanol

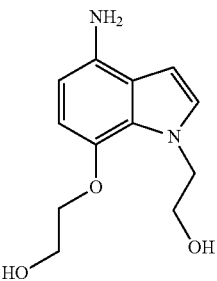

2-[4-amino-7-(2-hydroxyethoxy)-1H-indol-1-yl]ethanol

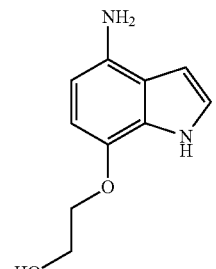

2-[(4-amino-1H-indol-7-yl)oxy]ethanol

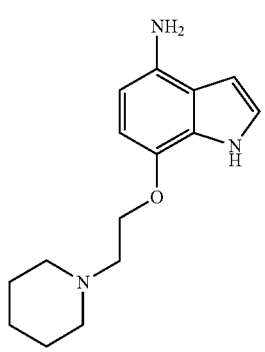

7-[2-(piperidin-1-yl)ethoxy]-1H-indol-4-amine

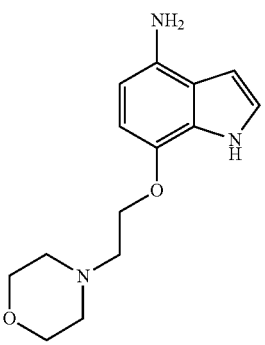

7-[2-(morpholin-4-yl)ethoxy]-1H-indol-4-amine

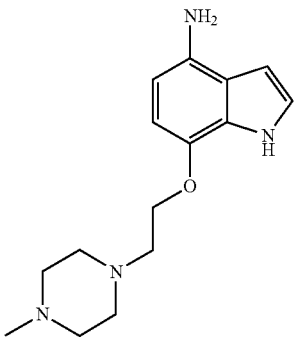

7-[2-(4-methylpiperazin-1-yl)ethoxy]-1H-indol-4-amine

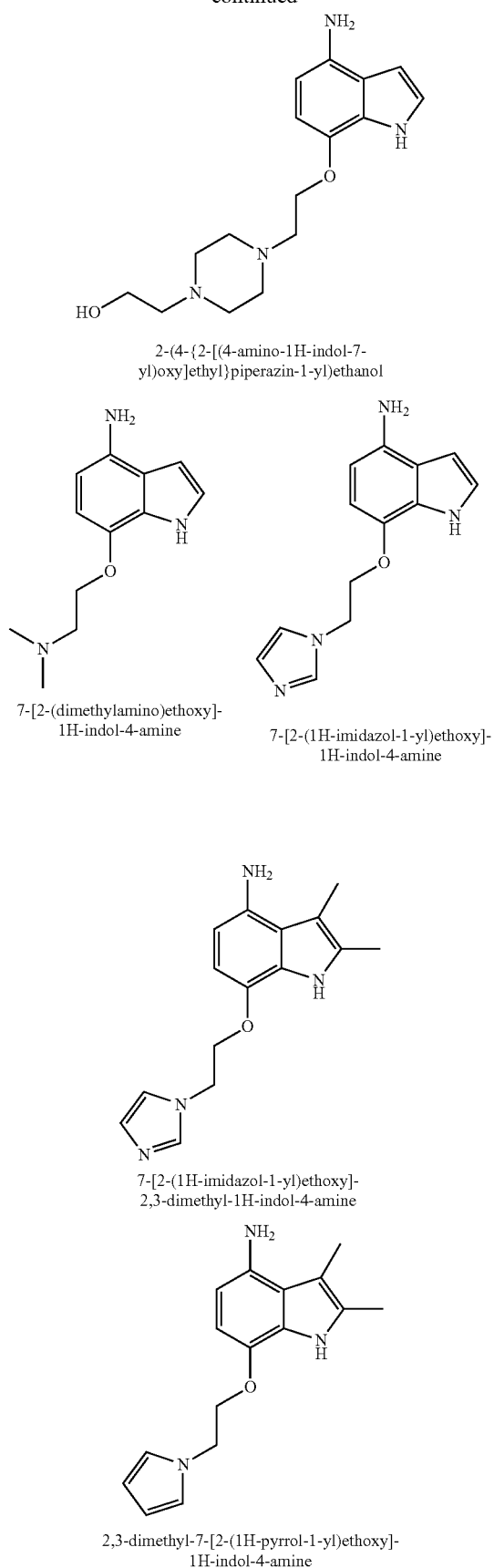

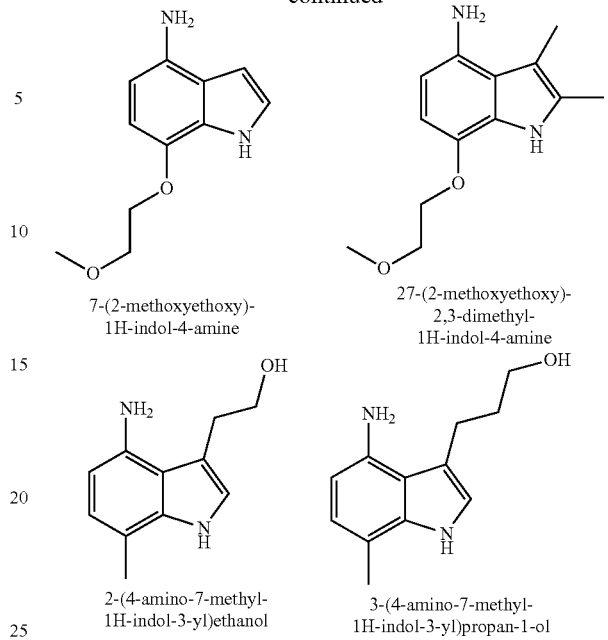

A subject of the present invention is also a composition for the oxidation dyeing of keratin fibres, comprising, in a suitable dyeing medium, at least one coupler chosen from the 4-aminoindole derivatives as defined previously.

The coupler(s) chosen from the 4-aminoindole derivatives of formula (I) as defined previously, and the addition salts thereof, mesomers thereof, isomers thereof and solvates thereof are each generally in an amount of between 0.001% and 10% by weight approximately and preferably between 0.005% and 6% by weight relative to the total weight of the dye composition.

According to one particular embodiment of the invention, the composition moreover comprises at least one oxidation base.

The oxidation base(s) present in the composition in accordance with the invention may be chosen from the oxidation bases conventionally used in oxidation dyeing. By way of example, these oxidation bases are chosen from para-phenylenediamines, bis(phenyl)alkylenediamines, para-aminophenols, bis-para-aminophenols, ortho-aminophenols, ortho-phenylenediamines and heterocyclic bases, and the addition salts thereof.

Among the para-phenylenediamines that may be mentioned, for example, are para-phenylenediamine, para-tolylenediamine, 2-chloro-para-phenylenediamine, 2,3-dimethyl-para-phenylenediamine, 2,6-dimethyl-para-phenylenediamine, 2,6-diethyl-para-phenylenediamine, 2,5-dimethyl-para-phenylenediamine, N,N-dimethyl-para-phenylenediamine, N,N-diethyl-para-phenylenediamine, N,N-dipropyl-para-phenylenediamine, 4-amino-N, N-diethyl-3-methylaniline, N,N-bis(β-hydroxyethyl)-para-phenylenediamine, 4-N,N-bis(β-hydroxyethyl)amino-2-methylaniline, 4-N,N-bis(β-hydroxyethyl)amino-2-chloroaniline, 2-β-hydroxyethyl-para-phenylenediamine, 2-fluoro-para-phenylenediamine, 2-isopropyl-para-phenylenediamine, N-(β-hydroxypropyl)-para-phenylenediamine, 2-hydroxymethyl-para-phenylenediamine, N,N-dimethyl-3-methyl-para-phenylenediamine, N-ethyl-N-(β-hydroxyethyl)-para-phenylenediamine, N-(β,γ-dihydroxypropyl)-para-phenylenediamine, N-(4'-aminophenyl)-paraphenylenediamine, N-phenyl-para-phenylenediamine, 2-β-hydroxyethyloxy-para-phenylenediamine, 2-β-acetylaminoethyloxy-para-phenylenediamine, N-(β-methoxyethyl)-para-phenylenediamine, 4-aminophenylpyrrolidine, 2-thienyl-para-phenylenediamine, 2-β-hydroxyethylamino-5-aminotoluene and 3-hydroxy-1-(4'-aminophenyl)pyrrolidine, and the addition salts thereof with an acid.

Among the para-phenylenediamines mentioned above, para-phenylenediamine, para-tolylenediamine, 2-isopropyl-para-phenylenediamine, 2-β-hydroxyethyl-para-phenylenediamine, 2-β-hydroxyethyloxy-para-phenylenediamine, 2,6-dimethyl-para-phenylenediamine, 2,6-diethyl-para-phenylenediamine, 2,3-dimethyl-para-phenylenediamine, N,N-bis(β-hydroxyethyl)-para-phenylenediamine, 2-chloro-para-phenylenediamine and 2-β-acetylaminoethyloxy-para-phenylenediamine, and the addition salts thereof with an acid, are particularly preferred.

Among the bis(phenyl)alkylenediamines that may be mentioned, for example, are N,N'-bis(β-hydroxyethyl)-N,N'-bis(4'-aminophenyl)-1,3-diaminopropanol, N,N'-bis(β-hydroxyethyl)-N,N'-bis(4'-aminophenyl)ethylenediamine, N,N'-bis(4-aminophenyl)tetramethylenediamine, N,N'-bis(β-hydroxyethyl)-N,N'-bis(4-aminophenyl)tetramethylenediamine, N,N'-bis(4-methylaminophenyl)tetramethylenediamine, N,N'-bis(ethyl)-N,N'-bis(4'-amino-3'-methylphenyl)ethylenediamine and 1,8-bis(2,5-diaminophenoxy)-3,6-dioxaoctane, and the addition salts thereof with an acid.

Among the para-aminophenols that may be mentioned, for example, are para-aminophenol, 4-amino-3-methylphenol, 4-amino-3-fluorophenol, 4-amino-3-hydroxymethylphenol, 4-amino-2-methylphenol, 4-amino-2-hydroxymethylphenol, 4-amino-2-methoxymethylphenol, 4-amino-2-aminomethylphenol, 4-amino-2-(β-hydroxyethylaminomethyl)phenol and 4-amino-2-fluorophenol, and the addition salts thereof with an acid.

Among the ortho-aminophenols that may be mentioned, for example, are 2-aminophenol, 2-amino-5-methylphenol, 2-amino-6-methylphenol and 5-acetamido-2-aminophenol, and the addition salts thereof with an acid.

Among the heterocyclic bases that may be mentioned, for example, are pyridine derivatives, pyrimidine derivatives and pyrazole derivatives.

Among the pyridine derivatives that may be mentioned are the compounds described, for example, in patents GB 1 026 978 and GB 1 153 196, for instance 2,5-diaminopyridine, 2-(4-methoxyphenyl)amino-3-aminopyridine, 2,3-diamino-6-methoxypyridine, 2-(β-methoxyethyl)amino-3-amino-6-methoxypyridine and 3,4-diaminopyridine, and the addition salts thereof with an acid.

Other pyridine oxidation bases that are useful in the present invention are the 3-aminopyrazolo[1,5-a]pyridine oxidation bases or the addition salts thereof described, for example, in patent application FR 2 801 308. Examples that may be mentioned include pyrazolo[1,5-a]pyrid-3-ylamine, 2-acetylaminopyrazolo[1,5-a]pyrid-3-ylamine, 2-morpholin-4-ylpyrazolo[1,5-a]pyrid-3-ylamine, 3-aminopyrazolo[1,5-a]pyridine-2-carboxylic acid, 2-methoxypyrazolo[1,5-a]pyrid-3-ylamine, (3-aminopyrazolo[1,5-a]pyrid-7-yl)methanol, 2-[(3-aminopyrazolo[1,5-a]pyrid-2-yl)oxy]ethanol, 2-(3-aminopyrazolo[1,5-a]pyrid-5-yl)ethanol, 2-(3-aminopyrazolo[1,5-a]pyrid-7-yl)ethanol, (3-aminopyrazolo[1,5-a]pyrid-2-yl)methanol, 3,6-diaminopyrazolo[1,5-a]pyridine, 3,4-diaminopyrazolo[1,5-a]pyridine, pyrazolo[1,5-a]pyridine-3,7-diamine, 7-morpholin-4-ylpyrazolo[1,5-a]pyrid-3-ylamine, pyrazolo[1,5-a]pyridine-3,5-diamine, 5-morpholin-4-ylpyrazolo[1,5-a]pyrid-3-ylamine, 2-[(3-aminopyrazolo[1,5-a]pyrid-5-yl)(2-hydroxyethyl)amino]ethanol, 2-[(3-aminopyrazolo[1,5-a]pyrid-7-yl)(2-hydroxyethyl)amino]ethanol, 3-aminopyrazolo[1,5-a]pyridin-5-ol, 3-aminopyrazolo[1,5-a]pyridin-4-ol, 3-aminopyrazolo[1,5-a]pyridin-6-ol, 3-aminopyrazolo[1,5-a]pyridin-7-ol and 4-(3-aminopyrazolo[1,5-a]pyridin-2-yl)-1,1-dimethylpiperazin-1-ium chloride and the addition salts thereof.

Among the pyrimidine derivatives that may be mentioned are the compounds described, for example, in patents DE 2 359 399; JP 88-169 571; JP 05-63124; EP 0 770 375 or patent application WO 96/15765, for instance 2,4,5,6-tetraminopyrimidine, 4-hydroxy-2,5,6-triaminopyrimidine, 2-hydroxy-4,5,6-triaminopyrimidine, 2,4-dihydroxy-5,6-diaminopyrimidine and 2,5,6-triaminopyrimidine, pyrazolopyrimidine derivatives such as those mentioned in patent application FR-A-2 750 048, and among which mention may be made of pyrazolo[1,5-a]pyrimidine-3,7-diamine, 2,5-dimethylpyrazolo[1,5-a]pyrimidine-3,7-diamine, pyrazolo[1,5-a]pyrimidine-3,5-diamine, 2,7-dimethylpyrazolo[1,5-a]pyrimidine-3,5-diamine, 3-aminopyrazolo[1,5-a]pyrimidin-7-ol, 3-aminopyrazolo[1,5-a]pyrimidin-5-ol, 2-(3-aminopyrazolo[1,5-a]pyrimidin-7-ylamino)ethanol, 2-(7-aminopyrazolo[1,5-a]pyrimidin-3-ylamino)ethanol, 2-[(3-aminopyrazolo[1,5-a]pyrimidin-7-yl)(2-hydroxyethyl)amino]ethanol, 2-[(7-aminopyrazolo[1,5-a]pyrimidin-3-yl)(2-hydroxyethyl)amino]ethanol, 5,6-dimethylpyrazolo[1,5-a]pyrimidine-3,7-diamine, 2,6-dimethylpyrazolo[1,5-a]pyrimidine-3,7-diamine, 2,5,-N7,N7-tetramethylpyrazolo[1,5-a]pyrimidine-3,7-diamine and 3-amino-5-methyl-7-imidazolylpropylaminopyrazolo[1,5-a]pyrimidine, and the addition salts thereof, and the tautomeric forms thereof, when a tautomeric equilibrium exists.

Among the pyrazole derivatives that may be mentioned are the compounds described in the patents DE 3843892, DE 4133957 and patent applications WO 94/08969, WO 94/08970, FR-A-2 733 749 and DE 195 43 988, such as 4,5-diamino-1-methylpyrazole, 4,5-diamino-1-(β-hydroxyethyl)pyrazole, 3,4-diaminopyrazole, 4,5-diamino-1-(4'-chlorobenzyl)-pyrazole, 4,5-diamino-1,3-dimethylpyrazole, 4,5-diamino-3-methyl-1-phenylpyrazole, 4,5-diamino-1-methyl-3-phenylpyrazole, 4-amino-1,3-dimethyl-5-hydrazinopyrazole, 1-benzyl-4,5-diamino-3-methylpyrazole, 4,5-diamino-3-tert-butyl-1-methylpyrazole, 4,5-diamino-1-tert-butyl-3-methylpyrazole, 4,5-diamino-1-(β-hydroxyethyl)-3-methylpyrazole, 4,5-diamino-1-ethyl-3-methylpyrazole, 4,5-diamino-1-ethyl-3-(4'-methoxyphenyl)pyrazole, 4,5-diamino-1-ethyl-3-hydroxymethylpyrazole, 4,5-diamino-3-hydroxymethyl-1-methylpyrazole, 4,5-diamino-3-hydroxymethyl-1-isopropylpyrazole, 4,5-diamino-3-methyl-1-isopropylpyrazole, 4-amino-5-(2'-aminoethyl)amino-1,3-dimethylpyrazole, 3,4,5-triaminopyrazole, 1-methyl-3,4,5-triamino-pyrazole, 3,5-diamino-1-methyl-4-methylaminopyrazole, 3,5-diamino-4-(β-hydroxyethyl)-amino-1-methylpyrazole, 2,3-diamino-6,7-dihydro-1H,5H-pyrazolo[1,2-a]pyrazol-1-one and the addition salts thereof. 4,5-Diamino-1-(β-methoxyethyl)pyrazole may also be used. A 4,5-diaminopyrazole will preferably be used, and even more preferentially 4,5-diamino-1-(β-hydroxyethyl)pyrazole and/or a salt thereof.

Pyrazole derivatives that may also be mentioned include diamino-N,N-dihydro-pyrazolopyrazolones and especially those described in patent application FR-A-2 886 136, such as the following compounds and the addition salts thereof: 2,3-diamino-6,7-dihydro-1H,5H-pyrazolo[1,2-a]pyrazol-1-one, 2-amino-3-ethylamino-6,7-dihydro-1H,5H-pyrazolo[1,2-a]pyrazol-1-one, 2-amino-3-isopropylamino-6,7-dihydro-1H,5H-pyrazolo[1,2-a]pyrazol-1-one, 2-amino-3-(pyrrolidin-1-yl)-6,7-dihydro-1H,5H-pyrazolo[1,2-a]pyrazol-1-one, 4,5-diamino-1,2-dimethyl-1,2-dihydropyrazol-3-one, 4,5-diamino-1,2-diethyl-1,2-dihydropyrazol-3-one, 4,5-diamino-1,2-di-(2-hydroxyethyl)-1,2-dihydropyrazol-3-one, 2-amino-3-(2-hydroxyethyl)amino-6,7-dihydro-1H,5H-pyrazolo[1,2-a]pyrazol-1-one, 2-amino-3-dimethylamino-6, 7-dihydro-1H,5H-pyrazolo[1,2-a]pyrazol-1-one, 2,3-diamino-5,6,7,8-tetrahydro-1H,6H-pyridazino[1,2-a]pyrazol-1-one, 4-amino-1,2-diethyl-5-(pyrrolidin-1-yl)-1,2-dihydropyrazol-3-one, 4-amino-5-(3-dimethylaminopyrrolidin-1-yl)-1,2-diethyl-1,2-dihydropyrazol-3-one, 2,3-diamino-6-hydroxy-6,7-dihydro-1H,5H-pyrazolo[1,2-a]pyrazol-1-one. 2,3-Diamino-6,7-dihydro-1H,5H-pyrazolo[1,2-a]pyrazol-1-one and/or a salt thereof will preferably be used.

Heterocyclic bases that will preferentially be used include 4,5-diamino-1-(β-hydroxyethyl)pyrazole and/or 2,3-diamino-6,7-dihydro-1H,5H-pyrazolo[1,2-a]pyrazol-1-one and/or 2-[(3-aminopyrazolo[1,5-a]pyridin-2-yl)oxy]ethanol and/or 4-(3-aminopyrazolo[1,5-a]pyridin-2-yl)-1,1-dimethylpiperazin-1-ium chloride and/or 1-{2-[(3-aminopyrazolo[1,5-a]pyridin-2-yl)amino]ethyl}-3-methyl-1H-imidazol-3-ium chloride and/or 2-[(3-aminopyrazolo[1,5-a]pyridin-2-yl)oxy]-N,N,N-trimethylethanaminium chloride and/or a salt thereof.

More preferentially, use will be made of 2,3-diamino-6,7-dihydro-1H,5H-pyrazolo[1,2-a]pyrazol-1-one and/or 2,3-diamino-5,6,7,8-tetrahydro-1H-pyrazolo[1,2-a]pyridazin-1-one and/or 2-[(3-aminopyrazolo[1,5-a]pyridin-2-yl)oxy]ethanol and/or 4-(3-aminopyrazolo[1,5-a]pyridin-2-yl)-1,1-dimethylpiperazin-1-ium chloride and/or 1-{2-[(3-aminopyrazolo[1,5-a]pyridin-2-yl)amino]ethyl}-3-methyl-1H-imidazol-3-ium chloride and/or 2-[(3-aminopyrazolo[1,5-a]pyridin-2-yl)oxy]-N,N,N-trimethylethanaminium chloride and/or salts thereof.

Even more preferentially, use will be made of 2,3-diamino-6,7-dihydro-1H,5H-pyrazolo[1,2-a]pyrazol-1-one and/or 2,3-diamino-5,6,7,8-tetrahydro-1H-pyrazolo[1,2-a]pyridazin-1-one and/or salts thereof.

The oxidation base(s) are each generally present in the composition in accordance with the invention in an amount of between 0.001% and 10% by weight approximately and preferably between 0.005% and 6% by weight relative to the total weight of the dye composition.

The dye composition of the invention may contain one or more additional couplers other than the 4-aminoindole derivatives of formula (I) as defined previously, and also the addition salts thereof, mesomers thereof, isomers thereof and solvates thereof. These additional couplers may be chosen from the couplers conventionally used for the dyeing of keratin fibres. Among these couplers, mention may be made especially of meta-phenylenediamines, meta-aminophenols, meta-diphenols, naphthalene-based couplers and heterocyclic couplers, and the addition salts thereof.

Examples that may be mentioned include 2-methyl-5-aminophenol, 5-N-(β-hydroxyethyl)amino-2-methylphenol, 6-chloro-2-methyl-5-aminophenol, 3-aminophenol, 1,3-dihydroxybenzene, 1,3-dihydroxy-2-methylbenzene, 4-chloro-1,3-dihydroxybenzene, 2,4-diamino-1-(β-hydroxyethyloxy)benzene, 2-amino-4-(β-hydroxyethylamino)-1-methoxybenzene, 1,3-diaminobenzene, 1,3-bis(2,4-diaminophenoxy)propane, 3-ureidoaniline, 3-ureido-1-dimethylaminobenzene, sesamol, 1-β-hydroxyethylamino-3,4-methylenedioxybenzene, α-naphthol, 2-methyl-1-naphthol, 6-hydroxyindole, 4-hydroxyindole, 4-hydroxy-N-methylindole, 2-amino-3-hydroxypyridine, 6-hydroxybenzomorpholine 3,5-diamino-2,6-dimethoxypyridine, 1-N-(β-hydroxyethyl)amino-3,4-methylenedioxybenzene and 2,6-bis(β-hydroxyethylamino)toluene, and the addition salts thereof with an acid.

In the composition of the present invention, when they are present, the amount of each of the couplers is generally between 0.001% and 10% by weight approximately and preferably between 0.005% and 6% by weight relative to the total weight of the dye composition.

In general, the addition salts of the oxidation bases and couplers that may be used in the context of the invention are especially chosen from addition salts with an acid, such as hydrochlorides, hydrobromides, sulfates, citrates, succinates, tartrates, lactates, tosylates, benzenesulfonates, phosphates and acetates, and the addition salts with a base such as sodium hydroxide, potassium hydroxide, ammonia, amines or alkanolamines.

According to one particular embodiment, the composition in accordance with the invention comprises at least one heterocyclic oxidation base.

The dye composition in accordance with the invention may also contain one or more direct dyes that may be chosen especially from nitrobenzene dyes, azo direct dyes and methine direct dyes. These direct dyes may be of nonionic, anionic or cationic nature.

The suitable dyeing medium, also known as the dye support, is a cosmetic medium generally consisting of water or a mixture of water and at least one organic solvent to dissolve the compounds that are not sufficiently water-soluble. Examples of organic solvents that may be mentioned include $C_1$-$C_4$ lower alkanols, such as ethanol and isopropanol; polyols and polyol ethers, for instance 2-butoxyethanol, propylene glycol, propylene glycol monomethyl ether, diethylene glycol monoethyl ether and monomethyl ether, and also aromatic alcohols, for instance benzyl alcohol or phenoxyethanol, and mixtures thereof.

The solvents are preferably present in proportions preferably of between 1% and 40% by weight approximately and even more preferably between 5% and 30% by weight approximately relative to the total weight of the dye composition.

The dye composition in accordance with the invention may also contain various adjuvants conventionally used in hair dye compositions, such as anionic, cationic, nonionic, amphoteric or zwitterionic surfactants or mixtures thereof, anionic, cationic, nonionic, amphoteric or zwitterionic polymers or mixtures thereof, mineral or organic thickeners, and in particular anionic, cationic, nonionic and amphoteric polymeric associative thickeners, antioxidants, penetrants, sequestrants, fragrances, buffers, dispersants, conditioning agents, for instance volatile or non-volatile, modified or unmodified silicones, film-forming agents, ceramides, preserving agents and opacifiers.

The above adjuvants are generally present in an amount, for each of them, of between 0.01% and 20% by weight relative to the weight of the dye composition.

Needless to say, a person skilled in the art will take care to select this or these optional additional compound(s) such that the advantageous properties intrinsically associated with the oxidation dye composition in accordance with the invention are not, or are not substantially, adversely affected by the envisaged addition(s).

The pH of the dye composition in accordance with the invention is generally between 3 and 12 approximately and preferably between 5 and 11 approximately. It may be adjusted to the desired value by means of acidifying or basifying agents usually used in the dyeing of keratin fibres, or alternatively using standard buffer systems.

Among the acidifying agents that may be mentioned, for example, are mineral or organic acids, for instance hydrochloric acid, orthophosphoric acid or sulfuric acid, carboxylic acids, for instance acetic acid, tartaric acid, citric acid and lactic acid, and sulfonic acids.

Among the basifying agents that may be mentioned, for example, are aqueous ammonia, alkaline carbonates, alkanolamines such as monoethanolamine, diethanolamine and triethanolamine and derivatives thereof, sodium hydroxide, potassium hydroxide and the compounds of formula (II) below:

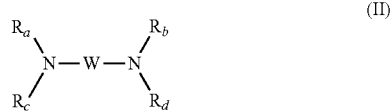

(II)

in which W is a propylene residue optionally substituted with a hydroxyl group or a $C_1$-$C_4$ alkyl radical; and $R_a$, $R_b$, $R_c$ and $R_d$, which may be identical or different, represent a hydrogen atom or a $C_1$-$C_4$ alkyl or $C_1$-$C_4$ hydroxyalkyl radical.

The dye composition according to the invention may be in various forms, such as in the form of liquids, creams or gels, or in any other form that is suitable for dyeing keratin fibres, and especially human hair.

The process of the present invention is a process for dyeing keratin fibres in which the composition according to the present invention as defined previously is applied to the fibres, and the colour is revealed using an oxidizing agent. The colour may be revealed at acidic, neutral or alkaline pH, and the oxidizing agent may be added to the composition of the invention right at the time of use, or it may be used starting with an oxidizing composition containing it, which is applied simultaneously with or sequentially to the composition of the invention.

In one particular embodiment the composition according to the present invention is mixed, preferably at the time of use, into a composition containing, in a medium appropriate for dyeing, at least one oxidizing agent, this oxidizing agent being present in an amount sufficient to develop a coloration. The mixture obtained is then applied to the keratin fibres. After a contact time of approximately 3 to 50 minutes, preferably approximately 5 to 30 minutes, the keratin fibres are rinsed, washed with shampoo, rinsed again and then dried.

The oxidizing agents conventionally used for the oxidation dyeing of keratin fibres are, for example, hydrogen peroxide, urea peroxide, alkali metal bromates, persalts such as perborates and persulfates, peracids and oxidase enzymes, among which mention may be made of peroxidases, two-electron oxidoreductases such as uricases, and four-electron oxygenases, for instance laccases. Hydrogen peroxide is particularly preferred.

The oxidizing composition may also contain various adjuvants conventionally used in compositions for dyeing the hair and as defined above.

The pH of the oxidizing composition containing the oxidizing agent is such that, after mixing with the dye composition, the pH of the resulting composition applied to the keratin fibres preferably ranges between 3 and 12 approximately and even more preferentially between 5 and 11. It may be adjusted to the desired value by means of acidifying or basifying agents usually used in the dyeing of keratin fibres and as defined previously.

The ready-to-use composition that is finally applied to the keratin fibres may be in various forms, such as in the form of liquids, creams or gels or in any other form that is suitable for the dyeing of keratin fibres, and in particular human hair.

A subject of the invention is also a multi-compartment dyeing device or kit in which a first compartment contains the dye composition of the present invention defined above and a second compartment contains an oxidizing composition. This device may be equipped with a means for dispensing the desired mixture on the hair, such as the devices described in patent FR-2 586 913 in the name of the Applicant.

Using this device, it is possible to dye the keratin fibres by means of a process which includes mixing a dye composition optionally comprising at least one oxidation base and at least one coupler of formula (I) with an oxidizing agent as defined above, and applying the resulting mixture to the keratin fibres for a time that is sufficient to develop the desired coloration.

A subject of the present invention is also the use of a composition for the oxidation dyeing of keratin fibres, and in particular human keratin fibres such as the hair, of at least one compound chosen from the 4-aminoindole derivatives of formula (I) as defined previously, the addition salts thereof, mesomers thereof, isomers thereof and solvates thereof.

According to one particular embodiment, the synthesis of the compounds of formula (I) is performed according to the following scheme:

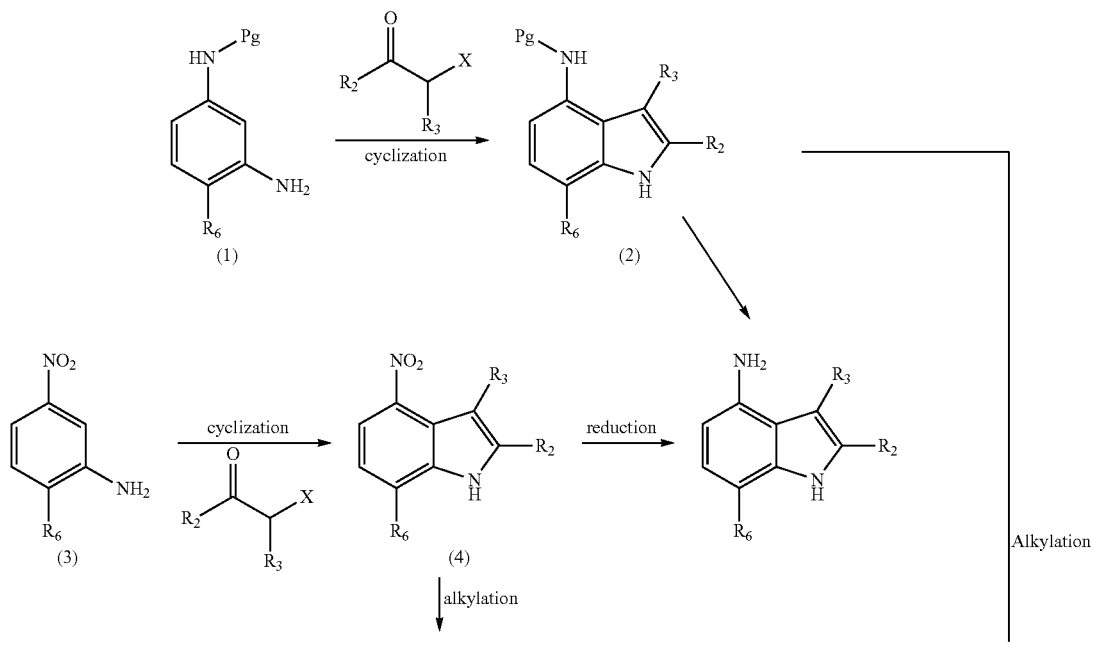

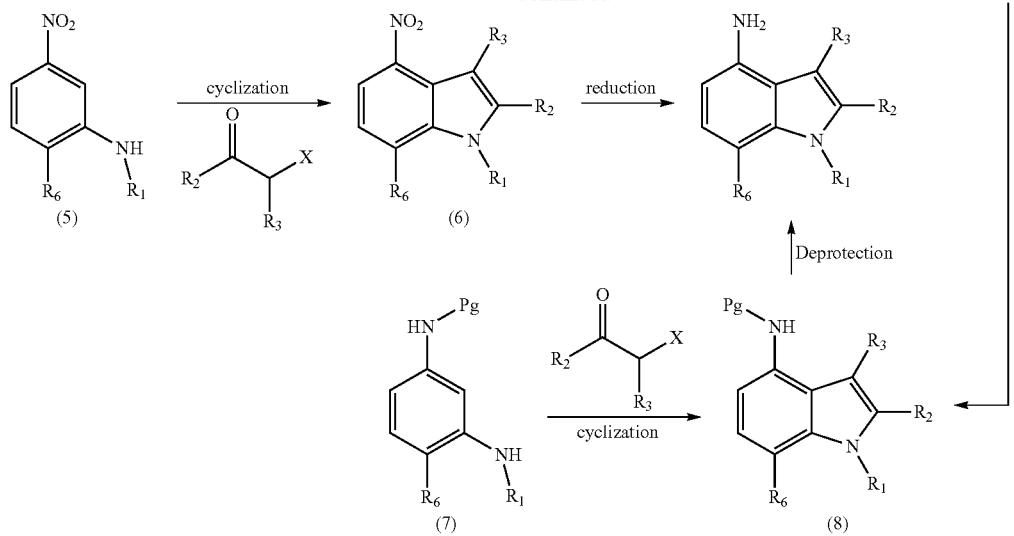

in which:
Pg is a protecting group for the amine function chosen from those mentioned in the publication *Protective Groups in Organic Synthesis*, T. W. Greene, P. G. M. Wutz, John Wiley & Sons, 2nd Ed, 1991;

X denotes a halogen atom such as a fluorine, chlorine, bromine or iodine atom.

According to another particular embodiment, the synthesis of the compounds of formula (I) is performed according to the following scheme:

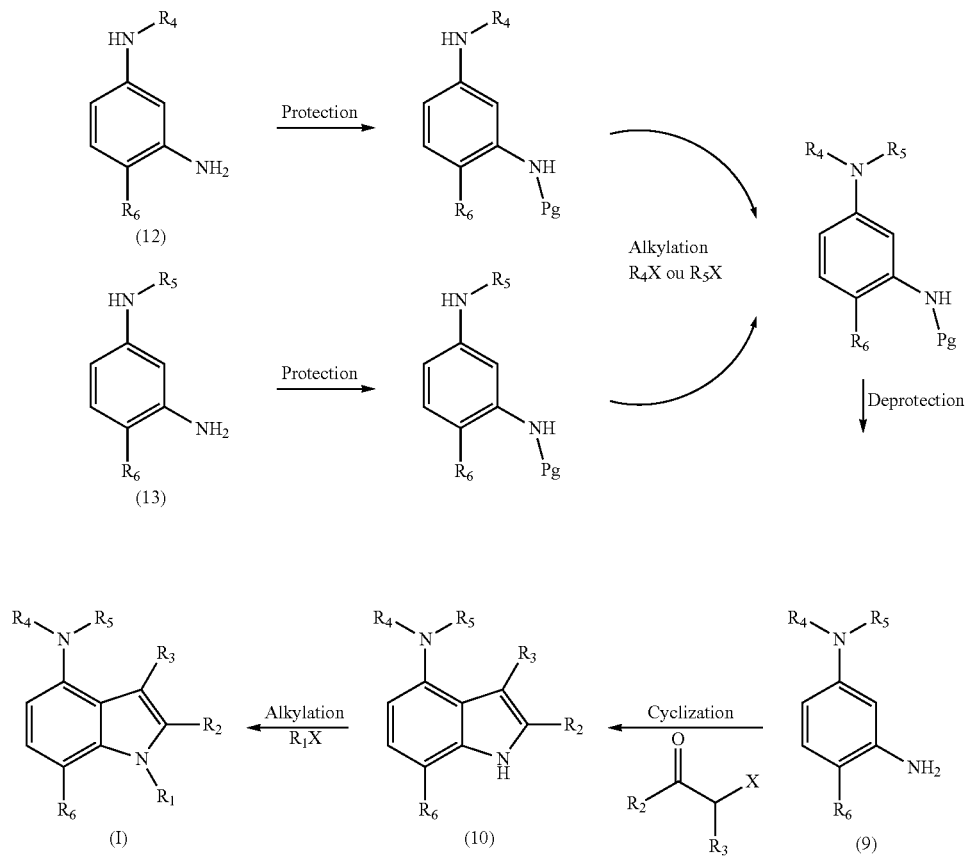

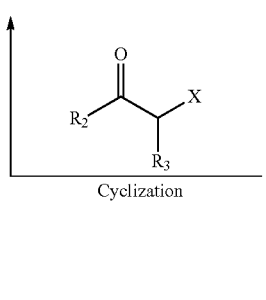 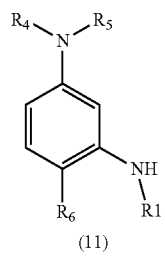 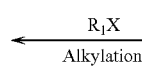

Cyclization | (11) | Alkylation

The compounds (2) are obtained from the protected amines (1) via a cyclization reaction of Bischler type performed in a dipolar solvent such as DMF, NMP, acetonitrile or THF, or in an alcohol such as ethanol, for example, optionally in the presence of an organic or mineral base such as triethylamine, ethyldiisopropylamine, sodium hydroxide or potassium hydroxide, with 0.5 to 1 or more equivalents of carbonyl halide $R_2$—CO—CHX—$R_3$ for 1 to 24 hours at a temperature ranging from 20° C. to the reflux temperature of the solvent. The cyclization reactions of (3) to lead to (4), or of (5) to lead to (6), or of (7) to lead to (8), or of (9) to lead to (10), or of (11) to lead to (I), are performed in the same manner.

The alkylation of compounds (4) is performed with at least one equivalent of alkyl halide $R_1$—X in a solvent such as THF or acetonitrile or dioxane or ethyl acetate, in the presence of an organic or mineral base such as triethylamine, ethyldiisopropylamine, sodium hydroxide or potassium hydroxide, for 15 minutes to 24 hours at a temperature ranging from 15° C. to the reflux temperature of the solvent and leads to compounds (6). The alkylation of compounds (2) to give compounds (8), or of (9) to give (11), or of (10) to give (I), is performed according to an identical protocol.

The reduction of the nitro group of the compounds (4) and (6) is performed under standard conditions, for example by performing a hydrogenation reaction under heterogeneous catalysis in the presence of a catalyst such as Pd/C, Pd(II)/C or Ni/Ra, or alternatively by performing a reduction reaction with a metal, for example with zinc, iron or tin (see *Advanced Organic Chemistry*, 3rd Edition, J. March, 1985, Wiley Interscience and *Reduction in Organic Chemistry*, M. Hudlicky, 1983, Ellis Horwood Series Chemical Science).

The cleavage of the protecting group Pg may be performed in acidic or basic medium in a very conventional manner, depending on their nature (see *Protective Groups for Organic Synthesis*, T. W. Greene, P. G. M. Wutz, John Wiley & Sons, 2nd Ed, 1991).

When compounds (9) are not commercially available, they may be obtained, for example, from the diamines (12) or (13).

The examples that follow serve to illustrate the invention without, however, being limiting in nature.

EXAMPLES

Example 1 synthesis of 2,3,7-trimethyl-1H-indol-4-amine hydrochloride

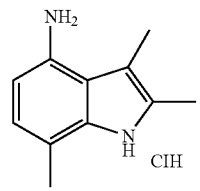

Step 1: synthesis of N-(2,3,7-trimethyl-1H-indol-4-yl)acetamide

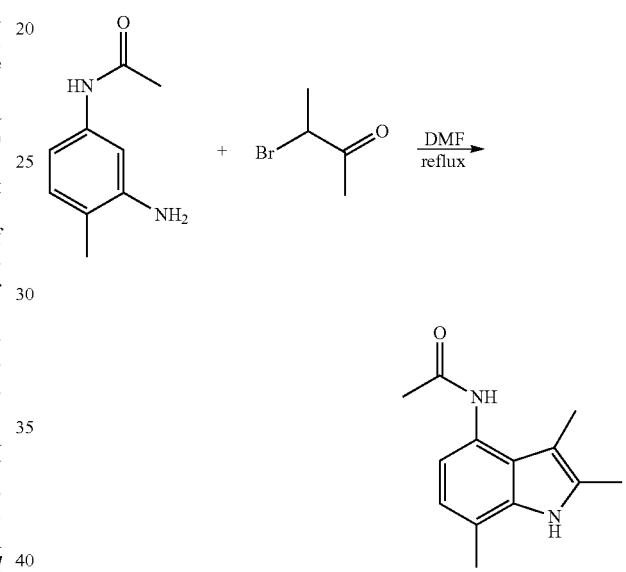

5 g (30 mmol) of N-(3-amino-4-methylphenyl)acetamide are placed in 12 ml of dimethylformamide in a 25 ml three-necked flask equipped with a condenser, a thermometer and a magnetic stirrer, and 3.24 ml (30 mmol) of 3-bromo-2-butanone are added dropwise. The mixture is then maintained at 100° C. for 8 hours until the starting material has totally disappeared.

The reaction medium is cooled and then poured into a mixture of ice and water. The gummy precipitate formed is taken up in dichloromethane.

The organic phase is then washed with water, after which it is dried over sodium sulfate, and the solvents are then removed on a rotary evaporator under vacuum.

The crude product thus obtained is purified by flash chromatography on a column of silica (eluent: dichloromethane) to give, after removal of the solvent, 1.4 g of a beige-coloured powder corresponding to the expected product (yield=21.2%).

The NMR analyses ($^1$H 400 MHz and $^{13}$C 100.61 MHz DMSO-$d_6$) are in accordance with the expected structure.

The analysis by mass spectrometry confirms the structure of the expected compound $C_{13}H_{16}N_2O$. The quasi-molecular ions [M+H]+, [M+Na]+, [M−H]− of the expected molecule are mainly detected.

Step 2: Synthesis of 2,3,7-trimethyl-1H-indol-4-amine

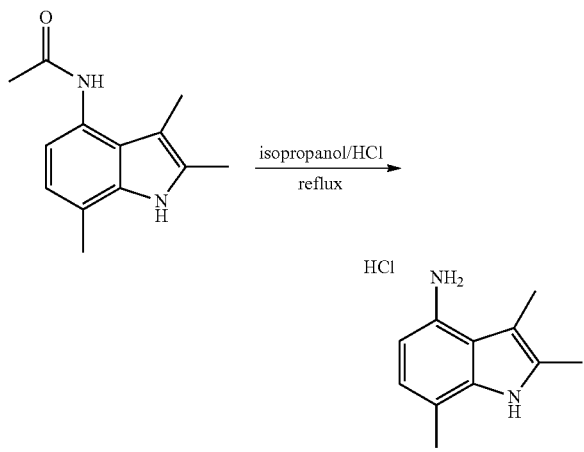

1.4 g (30 mmol) of N-(2,3,7-trimethyl-1H-indol-4-yl)acetamide are placed in 8 ml of a 50% solution of HCl in isopropanol in a 25 ml three-necked flask equipped with a condenser, a thermometer and a magnetic stirrer. The medium is refluxed for 48 hours.

The solvent is then removed under vacuum on a rotary evaporator to give 1.15 g of a grey powder corresponding to the expected compound (yield=64%).

The analysis by mass spectrometry confirms the expected structure $C_{11}H_{14}N_2$. The quasi-molecular ions [M+H]+, [M+Na]+, [M−H]− of the expected molecule are mainly detected.

Example 2 synthesis of 2,3-dimethyl-7-(propan-2-yl)-1H-indol-4-amine hydrochloride

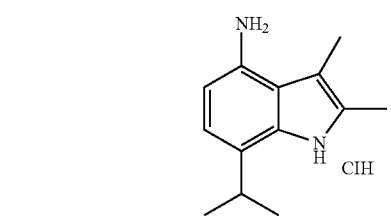

Step 1: synthesis of N[2,3-dimethyl-7-(propan-2-yl)-1H-indol-4-yl]acetamide

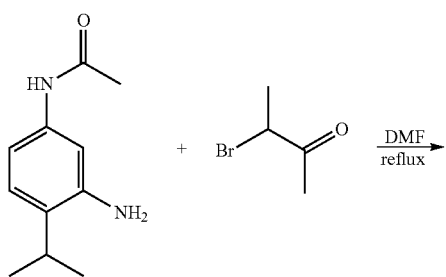

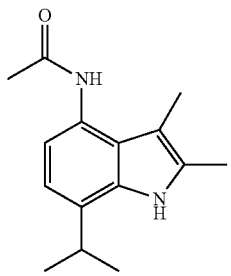

6.7 g (34.8 mmol) of N-[3-amino-4-(1-methylethyl)phenyl]acetamide are placed in 20 ml of dimethylformamide in a 25 ml three-necked flask equipped with a condenser, a thermometer and a magnetic stirrer, and 1.4 ml (13 mmol) of 3-bromo-2-butanone are then added dropwise.

The medium is then maintained at 100° C. for 48 hours, and is then cooled and poured into a mixture of ice and water, with stirring.

The precipitate formed is filtered off and washed thoroughly with water, and then dried under vacuum in the presence of a desiccant.

The crude product thus obtained is purified by flash chromatography on a column of silica (eluent: 95/5 dichloromethane/methanol) to give, after removal of the solvent, 2.87 g of a brown powder corresponding to the expected product (yield=51%).

The NMR analyses ($^1$H 400 MHz and $^{13}$C 100.61 MHz DMSO-$d_6$) are in accordance with the expected structure.

The analysis by mass spectrometry confirms the structure of the expected compound $C_{15}H_{20}N_2O$. The quasi-molecular ions [M+H]+, [M+Na]+, [M−H]− of the expected molecule are mainly detected.

Step 2: Synthesis of 2,3-dimethyl-7-(propan-2-yl)-1H-indol-4-amine hydrochloride

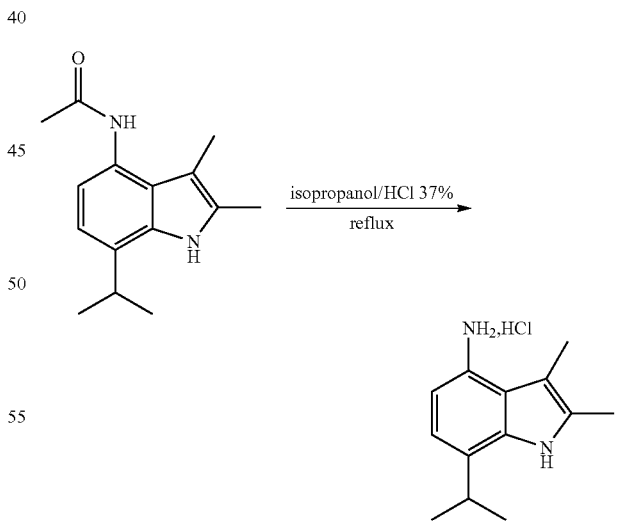

This compound is obtained according to a protocol identical to that described for Example 1, replacing the 6N HCl isopropanol solution with 6 ml of a 37.5% hydrochloric acid solution. For this example, the reaction of 2.87 g of N-[2,3-dimethyl-7-(propan-2-yl)-1H-indol-4-yl]acetamide leads to 2.8 g of a powder corresponding to the expected product (yield=89%).

The NMR analyses ($^1$H 400 MHz and $^{13}$C 100.61 MHz DMSO-$d_6$) are in accordance with the expected structure.

The analysis by mass spectrometry confirms the structure of the expected compound $C_{13}H_{18}N_2$. The quasi-molecular ions [M+H]+, [M+Na]+, [M−H]− of the expected molecule are mainly detected.

Examples of Dyeing

The following dye compositions are prepared:

| Example 3 | | | |
|---|---|---|---|
| 2,3,7-trimethyl-1H-indol-4-amine hydrochloride (Example 1) | $10^{-3}$ mol | $10^{-3}$ mol | $10^{-3}$ mol |
| 2,3-diamino-6,7-dihydro-1H,5H-pyrazolo[1,2-a]pyrazol-1-one dimethanesulfonate | $10^{-3}$ mol | — | — |
| 2-[(3-aminopyrazolo[1,5-a]pyridin-2-yl)oxy]ethanol hydrochloride | — | $10^{-3}$ mol | — |
| 4-(3-aminopyrazolo[1,5-a]pyridin-2-yl)-1,1-dimethylpiperazin-1-ium chloride hydrochloride | — | — | $10^{-3}$ mol |
| Dye support (1) Demineralized water qs | (*) 100 g | (*) 100 g | (*) 100 g |
| Shade observed | Yellow | Light brown | Blue chromatic |

| Example 4 | | | |
|---|---|---|---|
| 2,3-dimethyl-7-(propan-2-yl)-1H-indol-4-amine hydrochloride (Example 2) | $10^{-3}$ mol | $10^{-3}$ mol | $10^{-3}$ mol |
| 2,3-diamino-6,7-dihydro-1H,5H-pyrazolo[1,2-a]pyrazol-1-one dimethanesulfonate | $10^{-3}$ mol | — | — |
| 2-[(3-aminopyrazolo[1,5-a]pyridin-2-yl)oxy]ethanol hydrochloride | — | $10^{-3}$ mol | — |
| 4-(3-aminopyrazolo[1,5-a]pyridin-2-yl)-1,1-dimethylpiperazin-1-ium chloride hydrochloride | — | — | $10^{-3}$ mol |
| Dye support (1) Demineralized water qs | (*) 100 g | (*) 100 g | (*) 100 g |
| Shade observed | Light blond | Violet | Green-blue chromatic |

(*): Dye support (1) pH 9.5

| | |
|---|---|
| 96° ethyl alcohol | 20.8 g |
| 35% aqueous sodium metabisulfite solution | 0.23 g AM |
| Pentasodium salt of diethylenetriaminepentaacetic acid as an aqueous 40% solution | 0.48 g AM |
| $C_8$-$C_{10}$ alkyl polyglucoside as an aqueous 60% solution | 3.6 g AM |
| Benzyl alcohol | 2.0 g |
| Polyethylene glycol containing 8 ethylene oxide units | 3.0 g |
| $NH_4Cl$ | 4.32 g |
| Aqueous ammonia containing 20% $NH_3$ | 2.94 g |

AM = active material

At the time of use, each composition is mixed with an equal weight of 20-volumes aqueous hydrogen peroxide solution (6% by weight). A final pH of 9.5 is obtained.

Each mixture obtained is applied to locks of grey hair containing 90% white hairs. After a leave-on time of 30 minutes, the locks are rinsed, washed with a standard shampoo, rinsed again and then dried.

The invention claimed is:

1. A compound chosen from 4-aminoindole derivatives of formula (I) and the addition salts, mesomers, isomers, and solvates thereof:

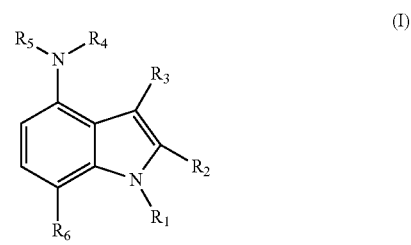

wherein:
$R_1$ is chosen from:
   hydrogen atoms; and
   linear and branched saturated $C_1$-$C_6$ alkyl radicals, optionally interrupted with a radical chosen from oxygen atoms and $NR_7$ radicals, optionally substituted with a radical chosen from OH and $NR_7R_8$;
$R_2$ and $R_3$, which may be identical or different, are chosen from:
   hydrogen atoms;
   $C_1$-$C_6$ alkyl radicals, optionally substituted with at least one hydroxyl radical;
   carboxyl radicals; and
   radicals $CONR_7R_8$;
$R_4$ and $R_5$, which may be identical or different, are chosen from:
   hydrogen atoms; and
   $C_1$-$C_6$ alkyl radicals;
$R_6$ is chosen from:
   linear and branched $C_1$-$C_6$ alkyl radicals, optionally interrupted with a heteroatom chosen from O and $NR_9$ radicals, and optionally substituted with at least one radical, which may be identical or different, chosen from OH and $NR_7R_8$;
   carboxyl radicals;
   $C_1$-$C_{10}$ alkyl carboxylates;
   radicals $CONR_7R_8$;
   $C_1$-$C_{10}$ (poly)hydroxyalkyloxy radicals;
   (poly)($C_1$-$C_{10}$)alkoxy($C_1$-$C_{10}$)alkyloxy radicals;
   —O-Ak-$NR_9R_{10}$ radicals wherein Ak is chosen from linear $C_1$-$C_8$ and branched $C_3$-$C_8$ divalent alkylene radicals, optionally interrupted with at least one oxygen atom and at least one group $NR_7$;
$R_7$ and $R_8$, which may be identical or different, are chosen from:
   hydrogen atoms;
   $C_1$-$C_8$ alkyl radicals optionally substituted with at least one hydroxyl radical;
$R_9$ and $R_{10}$, which may be identical or different, are chosen from linear and branched, saturated and unsaturated $C_1$-$C_4$ alkyls;
$R_9$ and $R_{10}$ may form, with the nitrogen that bears them, a saturated or unsaturated 5- to 8-membered heterocycle, one of the chain members optionally being chosen from oxygen atoms and $NR_{11}$ radicals wherein $R_{11}$ is chosen from hydrogen atoms and $C_1$-$C_4$ alkyls, optionally substituted with at least one radical chosen from OH and $NR_7R_8$;

with the exception of the two compounds:

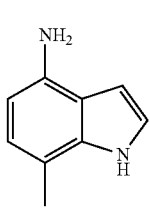 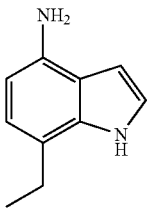

7-methyl-1H-indol-4-amine    7-ethyl-1H-indol-4-amine.

2. The compounds according to claim 1, wherein $R_1$ is chosen from hydrogen atoms and saturated $C_1$-$C_4$ alkyl radicals optionally substituted with a hydroxyl radical.

3. The compounds according to claim 1, wherein $R_2$ and $R_3$, which may be identical or different, are chosen from hydrogen atoms; $C_1$-$C_4$ alkyl radicals optionally substituted with at least one hydroxyl radical; carboxyl radicals; and radicals $CONR_7R_8$.

4. The compounds according to claim 3, wherein the radicals $CONR_7R_8$ are $CONH_2$.

5. The compounds according to claim 1, wherein $R_4$ and $R_5$ are identical and are hydrogen atoms.

6. The compounds according to claim 1, wherein $R_6$ is chosen from linear and branched $C_1$-$C_6$ alkyl radicals; carboxyl radicals; $C_1$-$C_6$ alkyl carboxylates; carboxamide radicals; $(C_1$-$C_6)$alkoxy$(C_1$-$C_6)$alkyloxy radicals; $C_1$-$C_6$ hydroxyalkyloxy radicals; and radicals O-Ak-$NR_6R_{10}$ wherein Ak is chosen from linear $C_1$-$C_6$ and branched $C_3$-$C_6$ divalent alkylene radicals optionally interrupted with a radical $NR_7$.

7. The compounds according to claim 1, wherein the 4-aminoindole derivatives of formula (I) are chosen from the derivatives of formula (I'):

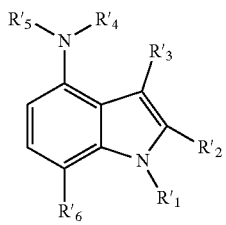

(I')

wherein:
$R'_1$ is chosen from:
  hydrogen atoms; and
  saturated $C_1$-$C_4$ alkyl radicals optionally substituted with a hydroxyl radical;
$R'_2$ and $R'_3$, which may be identical or different, are chosen from:
  hydrogen atoms;
  $C_1$-$C_4$ alkyl radicals optionally substituted with at least one hydroxyl radical;
  carboxyl radicals; and
  radicals $CONR'_7R'_8$;
$R'_4$ and $R'_5$ are hydrogen atoms;
$R'_6$ is chosen from:
  linear and branched $C_1$-$C_6$ alkyl radicals;
  carboxyl radicals;
  $C_1$-$C_6$ alkyl carboxylates;
  carboxamide radicals;
  radicals $(C_1$-$C_6)$alkoxy$(C_1$-$C_6)$alkyloxy;
  $C_1$-$C_6$ hydroxyalkyloxy radicals;

radicals O-Ak-$NR'_9R'_{10}$ wherein Ak is chosen from linear $C_1$-$C_6$ and branched $C_3$-$C_6$ divalent alkylene radicals, optionally interrupted with at least one oxygen atom and optionally interrupted with at least one group $NR'_7$;

$R'_7$ and $R'_8$ are chosen from hydrogen atoms and $C_1$-$C_6$ alkyl radicals optionally substituted with a hydroxyl radical;

$R'_9$ and $R'_{10}$, which may be identical or different, are chosen from saturated linear $C_1$-$C_4$ alkyl radicals and unsaturated linear $C_2$-$C_4$ alkyl radicals; and $R'_9$ and $R'_{10}$ may form, with the nitrogen that bears them, a saturated or unsaturated 5- to 8-membered heterocycle, one of the chain members optionally being chosen from oxygen atoms and radicals $NR'_{11}$ wherein $R'_{11}$ is chosen from hydrogen atoms and $C_1$-$C_4$ alkyls, optionally substituted with OH;

with the exception of the two compounds:

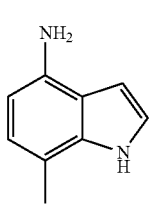 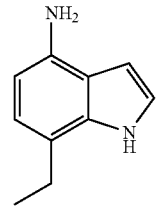

7-methyl-1H-indol-4-amine    7-ethyl-1H-indol-4-amine.

8. The compounds according to claim 1, wherein the radicals $CONR'_7R'_8$ are $CONH_2$.

9. The compounds according to claim 1, wherein the 4-aminoindole derivatives of formula (I) are chosen from:

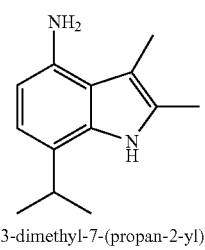 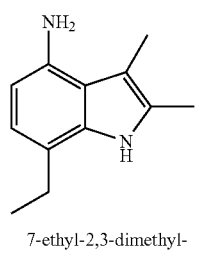

2,3-dimethyl-7-(propan-2-yl)-
1H-indol-4-amine 7-ethyl-2,3-dimethyl-
1H-indol-4-amine

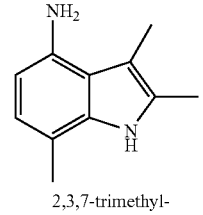

2,3,7-trimethyl-
1H-indol-4-amine 3-ethyl-2,7-dimethyl-
1H-indol-4-amine

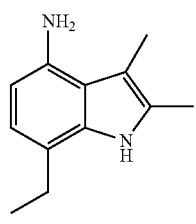 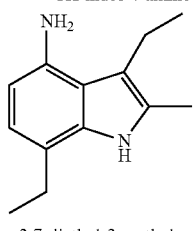

7-ethyl-2,3-dimethyl-
1H-indol-4-amine 3,7-diethyl-2-methyl-
1H-indol-4-amine

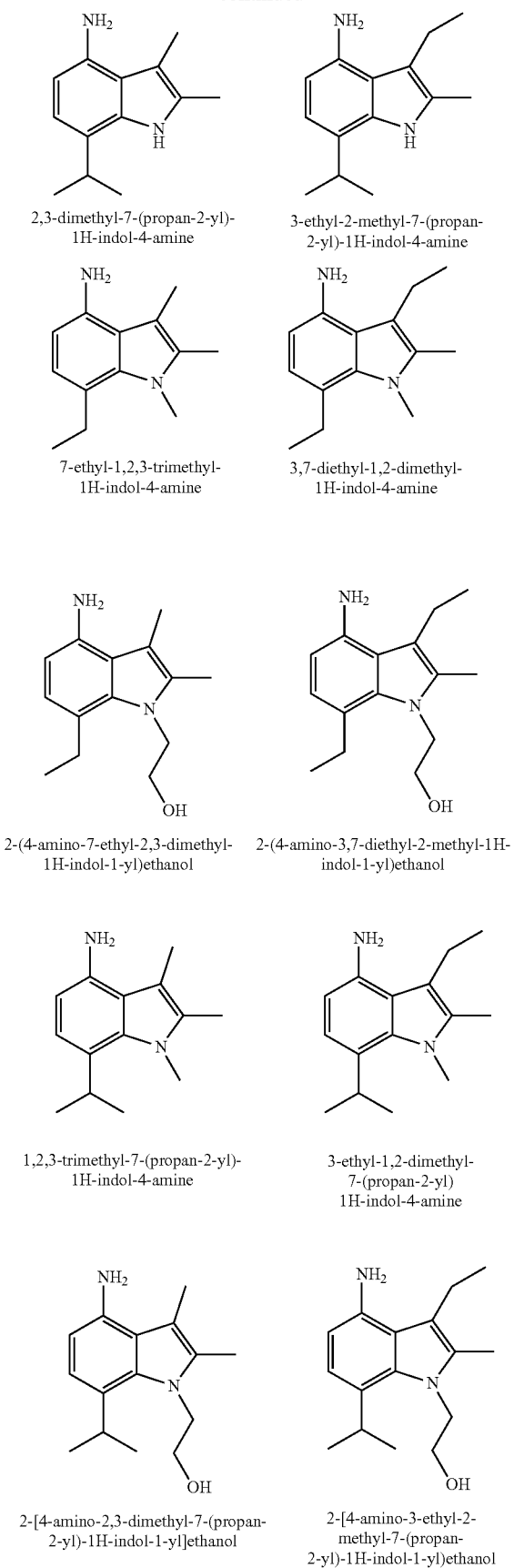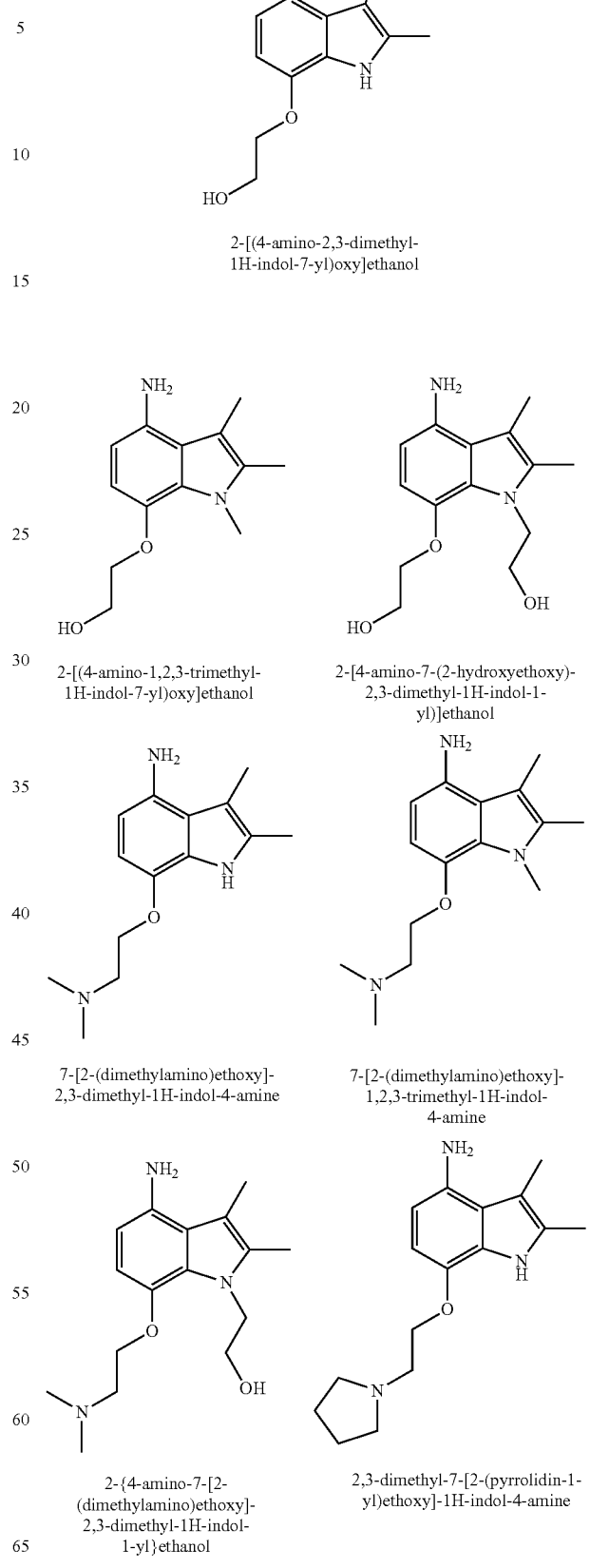

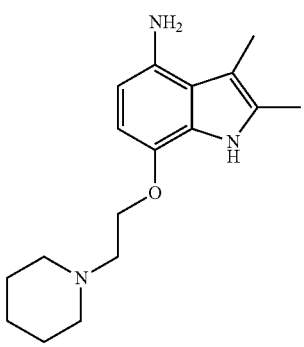

2,3-dimethyl-7-[2-(piperidin-1-yl)ethoxy]-1H-indol-4-amine

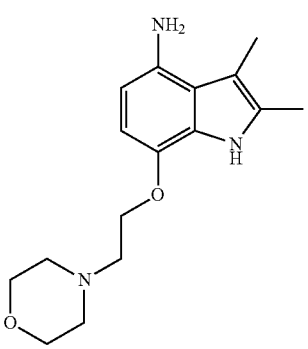

2,3-dimethyl-7-[2-(morpholin-4-yl)ethoxy]-1H-indol-4-amine

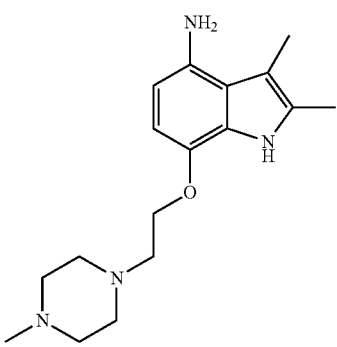

2,3-dimethyl-7-[2-(4-methylpiperazin-1-yl)ethoxy}-1H-indol-4-amine

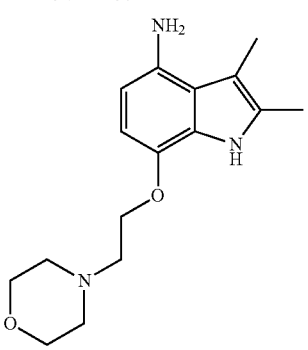

2,3-dimethyl-7-[2-(morpholin-4-yl)ethoxy]-1H-indol-4-amine

-continued

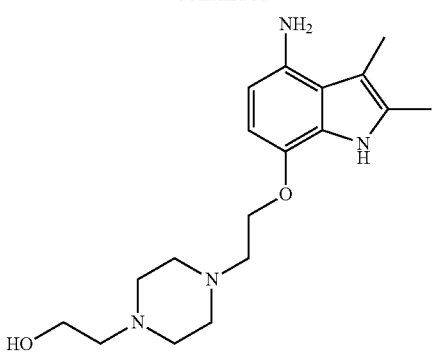

2-(4-{2-[(4-amino-2,3-dimethyl-1H-indol-7-yl)oxy]ethyl}piperazin-1-yl)ethanol

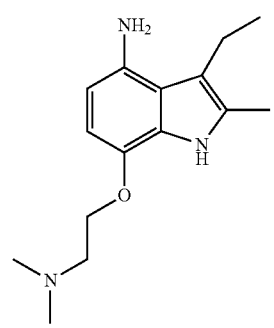

7-[2-(dimethylamino)ethoxy]-3-ethyl-2-methyl-1H-indol-4-amine

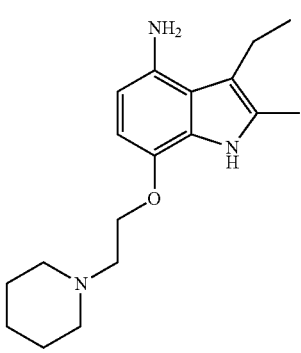

3-ethyl-2-methyl-7-[2-(piperidin-1-yl)ethoxy]-1H-indol-4-amine

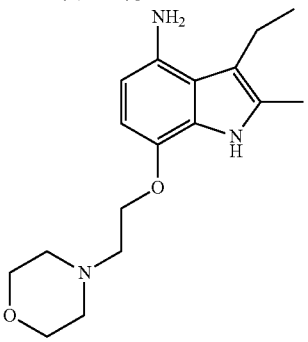

3-ethyl-2-methyl-7-[2-(morpholin-4-yl)ethoxy]-1H-indol-4-amine

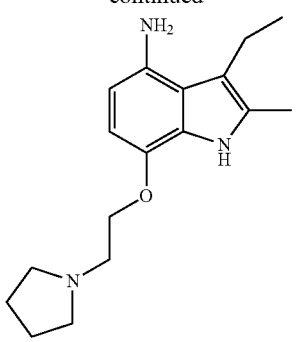

3-ethyl-2-methyl-7-[2-(pyrrolidin-1-yl)ethoxy]-1H-indol-4-amine

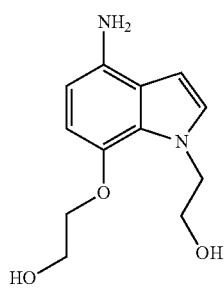

2-[4-amino-7-(2-hydroxyethoxy)-1H-indol-1-yl]ethanol

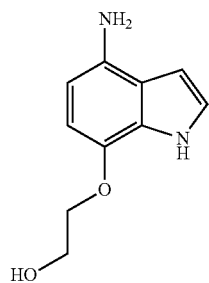

2-[(4-amino-1H-indol-7-yl)oxy]ethanol

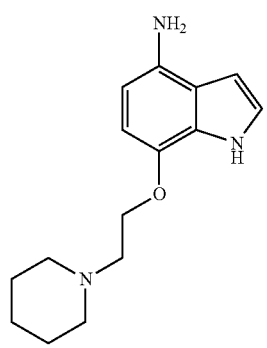

7-[2-(piperidin-1-yl)ethoxy]-1H-indol-4-amine

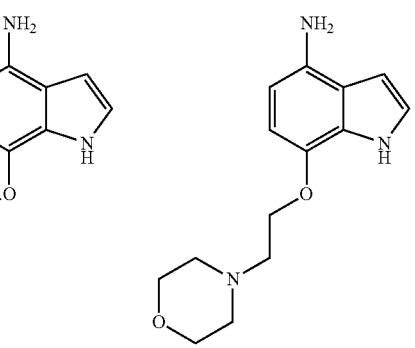

7-[2-(morpholin-4-yl)ethoxy]-1H-indol-4-amine

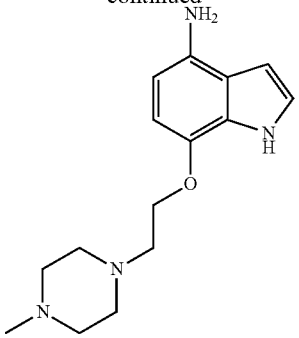

7-[2-(4-methylpiperazin-1-yl)ethoxy]-1H-indol-4-amine

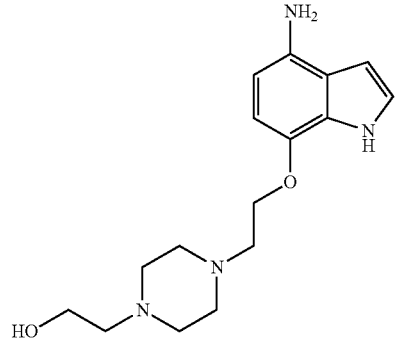

2-(4-{2-[(4-amino-1H-indol-7-yl)oxy]ethyl}piperazin-1-yl)ethanol

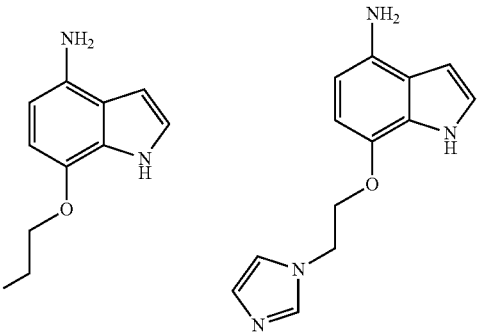

7-[2-(dimethylamino)ethoxy]-1H-indol-4-amine

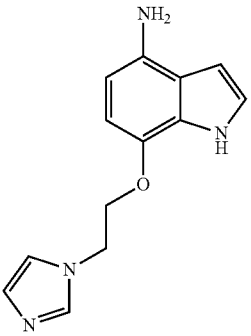

7-[2-(1H-imadazol-1-yl)ethoxy]-1H-indol-4-amine

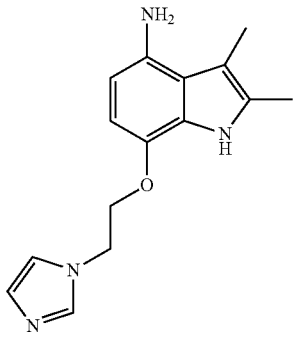

7-[2-(1H-imadazol-1-yl)ethoxy]-2,3-dimethyl-1H-indol-4-amine

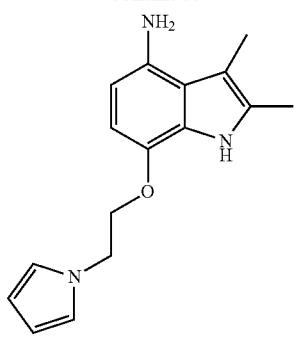

2,3-dimethyl-7-[2-(1H-pyrrol-1-yl)ethoxy]-1H-indol-4-amine

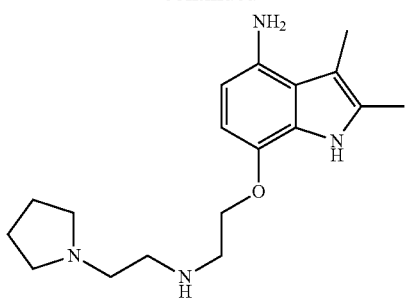

2,3-dimethyl-7-(2-{[2-(pyrrolidin-1-yl)ethyl]amino}ethoxy)-1H-indol-4-amine

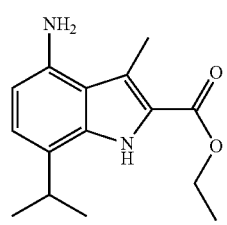

ethyl 4-amino-3-methyl-7-(propan-2-yl)-1H-indole-2-carboxylate

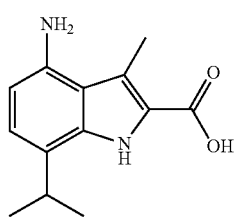

4-amino-7-(propan-2-yl)-1H-indole-2-carboxylic acid

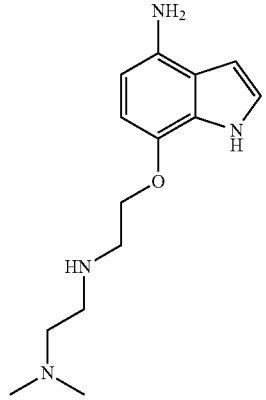

N'-{2-[(4-amino-1H-indol-7-yl)oxy]ethyl}-N,N-dimethylethane-1,2-diamine

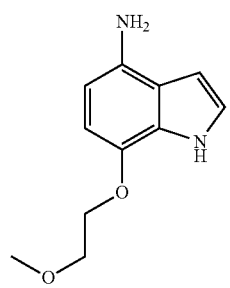

7-(2-methoxyethoxy)-1H-indol-4-amine

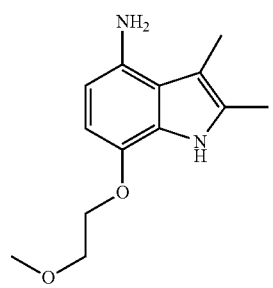

27-(2-methoxyethoxy)-2,3-dimethyl-1H-indol-4-amine

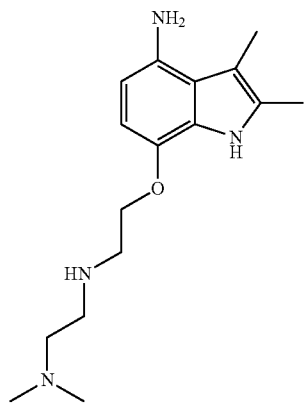

N'-{2-[(4-amino-2,3-dimethyl-1H-indol-7-yl)oxy]ethyl}-N,N-dimethylethane-1,2-diamine

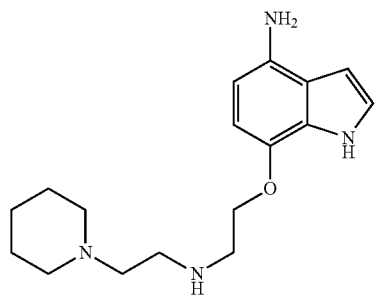

7-(2-{[2-(piperidin-1-yl)ethyl]amino}ethoxy)-1H-indol-4-amine

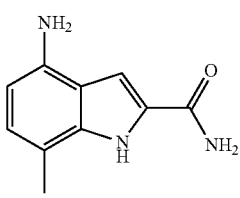

4-amino-3,7-dimethyl-1H-indole-2-carboxamide

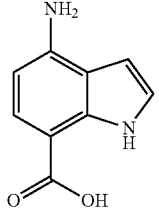

4-amino-1H-indole-7-carboxylic acid

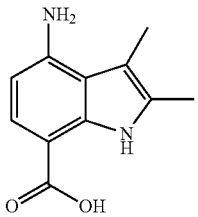

4-amino-2,3-dimethyl-1H-indole-7-carboxylic acid

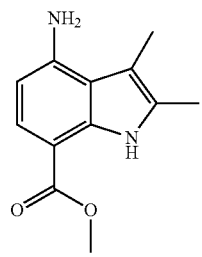

methyl-4-amino-2,3-dimethyl-1H-indole-7-carboxylate

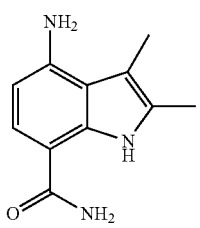

4-amino-2,3-dimethyl-1H-indole-7-carboxamide

4-amino-1H-indole-7-carboxamide.

10. A composition for the oxidation dyeing of keratin fibers, comprising, in a suitable dyeing medium, at least one coupler chosen from the compounds according to claim 1.

11. The composition according to claim 10, further comprising at least one oxidation base.

12. The composition according to claim 11, wherein the at least one oxidation base is chosen from para-phenylenediamines, bis(phenyl)alkylenediamines, para-aminophenols, bis-para-aminophenols, ortho-aminophenols, ortho-phenylenediamines, heterocyclic bases, and the addition salts thereof.

13. The composition according to claim 11, wherein the at least one oxidation base is a heterocyclic oxidation base.

14. The composition according to claim 13, wherein the heterocyclic base is chosen from at least one of 4,5-diamino-1-(β-hydroxyethyl)pyrazole, 2,3-diamino-6,7-dihydro-1H,5H-pyrazolo[1,2-a]pyrazol-1-one, 2-[(3-aminopyrazolo[1,5-a]pyridin-2-yl)oxy]ethanol, 4-(3-aminopyrazolo[1,5-a]pyridin-2-yl)-1,1-dimethylpiperazin-1-ium chloride, 1-{2-[(3-aminopyrazolo[1,5-a]pyridin-2-yl)amino]ethyl}-3-methyl-1H-imidazol-3-ium chloride 2-[(3-aminopyrazolo[1,5-a]pyridin-2-yl)oxy]-N,N,N-trimethylethanaminium chloride, and the salts thereof.

15. A process for dyeing keratin fibers, comprising applying to the keratin fibers, in the presence of an oxidizing agent, for a time sufficient to develop a desired coloration, a composition comprising at least one compound chosen from 4-aminoindole derivatives of formula (I) and the addition salts, mesomers, isomers, and solvates thereof:

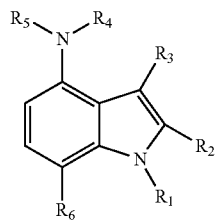

wherein:

$R_1$ is chosen from:

hydrogen atoms; and linear and branched saturated $C_1$-$C_6$ alkyl radicals, optionally interrupted with a radical chosen from oxygen atoms and $NR_7$ radicals, optionally substituted with a radical chosen from OH and $NR_7R_8$;

$R_2$ and $R_3$, which may be identical or different, are chosen from:

hydrogen atoms;

$C_1$-$C_6$ alkyl radicals, optionally substituted with at least one hydroxyl radical;

carboxyl radicals; and radicals $CONR_7R_8$;

$R_4$ and $R_5$, which may be identical or different, are chosen from:

hydrogen atoms; and $C_1$-$C_6$ alkyl radicals;

$R_6$ is chosen from:

linear and branched $C_1$-$C_6$ alkyl radicals, optionally interrupted with a heteroatom chosen from O and $NR_9$ radicals, and optionally substituted with at least one radical, which may be identical or different, chosen from OH and $NR_7R_8$;

carboxyl radicals;

$C_1$-$C_{10}$ alkyl carboxylates;

radicals $CONR_7R_8$;

$C_1$-$C_{10}$ (poly)hydroxyalkyloxy radicals;

(poly)($C_1$-$C_{10}$)alkoxy($C_1$-$C_{10}$)alkyloxy radicals;

—O-Ak-$NR_9R_{10}$ radicals wherein Ak is chosen from linear $C_1$-$C_8$ and branched $C_3$-$C_8$ divalent alkylene radicals, optionally interrupted with at least one oxygen atom and at least one group $NR_7$;

$R_7$ and $R_8$, which may be identical or different, are chosen from:

hydrogen atoms;

$C_1$-$C_8$ alkyl radicals optionally substituted with at least one hydroxyl radical;

$R_9$ and $R_{10}$, which may be identical or different, are chosen from linear and branched, saturated and unsaturated $C_1$-$C_4$ alkyls;

$R_9$ and $R_{10}$ may form, with the nitrogen that bears them, a saturated or unsaturated 5- to 8-membered heterocycle, one of the chain members optionally being chosen from oxygen atoms and $NR_{11}$ radicals wherein $R_{11}$ is chosen from hydrogen atoms and $C_1$-$C_4$ alkyls, optionally substituted with at least one radical chosen from OH and $NR_7R_8$;

with the exception of the two compounds:

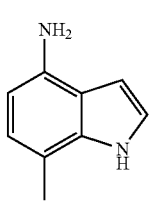 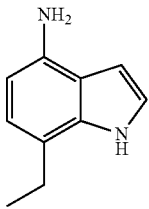

7-methyl-1H-indol-4-amine    7-ethyl-1H-indol-4-amine.

16. A multi-compartment device comprising:
a first compartment comprising a dye composition comprising at least one compound chosen from 4-aminoindole derivatives of formula (I) and the addition salts, mesomers, isomers, and solvates thereof:

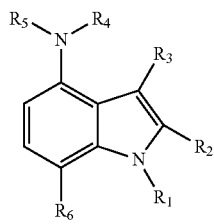

(I)

wherein:
$R_1$ is chosen from:
  hydrogen atoms; and
  linear and branched saturated $C_1$-$C_6$ alkyl radicals, optionally interrupted with a radical chosen from oxygen atoms and $NR_7$ radicals, optionally substituted with a radical chosen from OH and $NR_7R_8$;
$R_2$ and $R_3$, which may be identical or different, are chosen from:
  hydrogen atoms;
  $C_1$-$C_6$ alkyl radicals, optionally substituted with at least one hydroxyl radical;
  carboxyl radicals; and
  radicals $CONR_7R_8$;
$R_4$ and $R_5$, which may be identical or different, are chosen from:
  hydrogen atoms; and
  $C_1$-$C_6$ alkyl radicals;

$R_6$ is chosen from:
  linear and branched $C_1$-$C_6$ alkyl radicals, optionally interrupted with a heteroatom chosen from O and $NR_9$ radicals, and optionally substituted with at least one radical, which may be identical or different, chosen from OH and $NR_7R_8$;
  carboxyl radicals;
  $C_1$-$C_{10}$ alkyl carboxylates;
  radicals $CONR_7R_8$;
  $C_1$-$C_{10}$ (poly)hydroxyalkyloxy radicals;
  (poly)($C_1$-$C_{10}$)alkoxy($C_1$-$C_{10}$)alkyloxy radicals;
  —O-Ak-$NR_9R_{10}$ radicals wherein Ak is chosen from linear $C_1$-$C_8$ and branched $C_3$-$C_8$ divalent alkylene radicals, optionally interrupted with at least one oxygen atom and at least one group $NR_7$;
$R_7$ and $R_8$, which may be identical or different, are chosen from:
  hydrogen atoms;
  $C_1$-$C_8$ alkyl radicals optionally substituted with at least one hydroxyl radical;
$R_9$ and $R_{10}$, which may be identical or different, are chosen from linear and branched, saturated and unsaturated $C_1$-$C_4$ alkyls;
$R_9$ and $R_{10}$ may form, with the nitrogen that bears them, a saturated or unsaturated 5- to 8-membered heterocycle, one of the chain members optionally being chosen from oxygen atoms and $NR_{11}$ radicals wherein $R_{11}$ is chosen from hydrogen atoms and $C_1$-$C_4$ alkyls, optionally substituted with at least one radical chosen from OH and $NR_7R_8$;
with the exception of the two compounds:

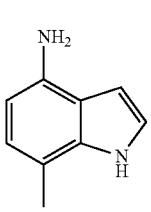 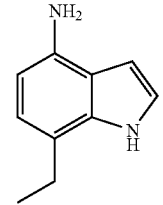

7-methyl-1H-indol-4-amine    7-ethyl-1H-indol-4-amine; and a second compartment comprising at least one oxidizing agent.

* * * * *